US012582606B2

(12) United States Patent
Sei et al.

(10) Patent No.: US 12,582,606 B2
(45) Date of Patent: *Mar. 24, 2026

(54) TABLET AND METHOD FOR PRODUCING TABLET

(71) Applicant: SUNSHO PHARMACEUTICAL CO., LTD., Fuji (JP)

(72) Inventors: Shunsuke Sei, Fujinomiya (JP);
Misuzu Mineda, Fujinomiya (JP);
Chikara Morizane, Fujinomiya (JP);
Wataru Hirasawa, Fujinomiya (JP)

(73) Assignee: SUNSHO PHARMACEUTICAL CO., LTD., Fuji (JP)

(*) Notice: Subject to any disclaimer, the term of this patent is extended or adjusted under 35 U.S.C. 154(b) by 1064 days.

This patent is subject to a terminal disclaimer.

(21) Appl. No.: 17/603,815

(22) PCT Filed: Apr. 14, 2020

(86) PCT No.: PCT/JP2020/016380
§ 371 (c)(1),
(2) Date: Oct. 14, 2021

(87) PCT Pub. No.: WO2020/213589
PCT Pub. Date: Oct. 22, 2020

(65) Prior Publication Data
US 2022/0218616 A1 Jul. 14, 2022

Related U.S. Application Data

(60) Provisional application No. 62/896,674, filed on Sep. 6, 2019, provisional application No. 62/834,177, filed on Apr. 15, 2019.

(51) Int. Cl.
*A61K 9/20* (2006.01)
*A61K 45/06* (2006.01)

(52) U.S. Cl.
CPC .......... *A61K 9/2095* (2013.01); *A61K 9/2018* (2013.01); *A61K 9/2081* (2013.01); *A61K 9/2086* (2013.01); *A61K 45/06* (2013.01)

(58) Field of Classification Search
CPC .. A61K 9/2095; A61K 9/2018; A61K 9/2081; A61K 9/2086; A61K 45/06
See application file for complete search history.

(56) References Cited

U.S. PATENT DOCUMENTS

| | | | |
|---|---|---|---|
| 2004/0175422 A1 | 9/2004 | Tomohira | |
| 2006/0104909 A1 | 5/2006 | Vaghefi et al. | |
| 2009/0246276 A1 * | 10/2009 | Jackson | A61P 25/24 |
| | | | 514/468 |
| 2020/0315962 A1 | 10/2020 | Endo | |
| 2021/0161820 A1 | 6/2021 | Sei | |

FOREIGN PATENT DOCUMENTS

| | | |
|---|---|---|
| CN | 103783476 A | 5/2014 |
| JP | H-0776517 A | 3/1996 |
| JP | H08332051 A | 12/1996 |
| JP | 2003-040764 A | 2/2003 |
| JP | 2017-210415 A | 11/2017 |
| JP | 6409937 B1 * | 10/2018 |
| JP | 2019-073459 A | 5/2019 |
| JP | 2019-182856 A | 10/2019 |
| JP | 2006502192 A | 1/2026 |
| WO | 2013-129644 A1 | 9/2013 |
| WO | 2019-198612 A1 | 10/2019 |

OTHER PUBLICATIONS

Hancock BC, Parks M. What is the true solubility advantage for amorphous pharmaceuticals? Pharm Res. Apr. 2000;17(4):397-404. doi: 10.1023/a:1007516718048. PMID: 10870982. (Year: 2000).*

Yasushi Ochiai, Small Particle Design for Advanced Functional Formulations—Creation and Evaluation of Opusgran-; The Micromeritics No. 61 (2018) pp. 28-34.

English Translation of International Preliminary Report on Patentability of PCT/JP2020/016380, Sep. 28, 2021.

International Search Report of PCT Application No. PCT/JP2020/016380, dated Jun. 9, 2020.

* cited by examiner

*Primary Examiner* — Frederick F Krass
*Assistant Examiner* — Abdulrahman Abbas
(74) *Attorney, Agent, or Firm* — RAPHAEL BELLUM PLLC

(57) ABSTRACT

Provided are a tablet and a method for producing the tablet, in particular, a technique for tablet production whereby the amount of an active ingredient to be contained in the tablet can be stably regulated without the need of a huge cost for the production. The tablet of the present invention is one obtained by compacting a mixture comprising a granulating composition including a medicinal ingredient or a biofunctional ingredient, and includes a first region, which comprises a binder including the medicinal ingredient or biofunctional ingredient, and a second region, which is adjacent to the first region and comprises the binder including the medicinal ingredient or biofunctional ingredient. The medicinal ingredient or biofunctional ingredient contained in each of the first region and second region is included in the binder, not in the form of a layer but in the state of having been dispersed or dissolved.

16 Claims, 5 Drawing Sheets

FIG.1

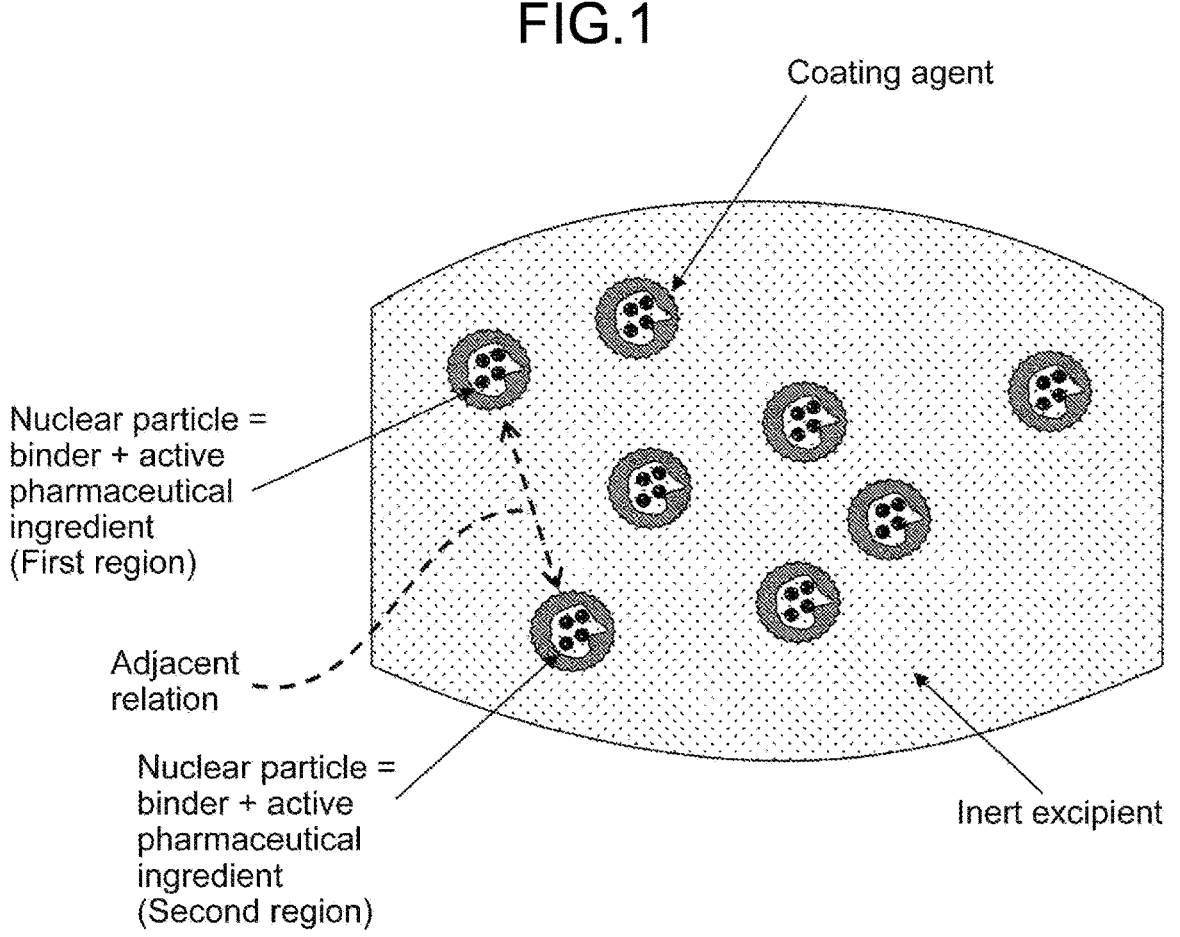

Coating agent

Nuclear particle =
binder + active
pharmaceutical
ingredient
(First region)

Adjacent
relation

Nuclear particle =
binder + active
pharmaceutical
ingredient
(Second region)

Inert excipient

FIG.2

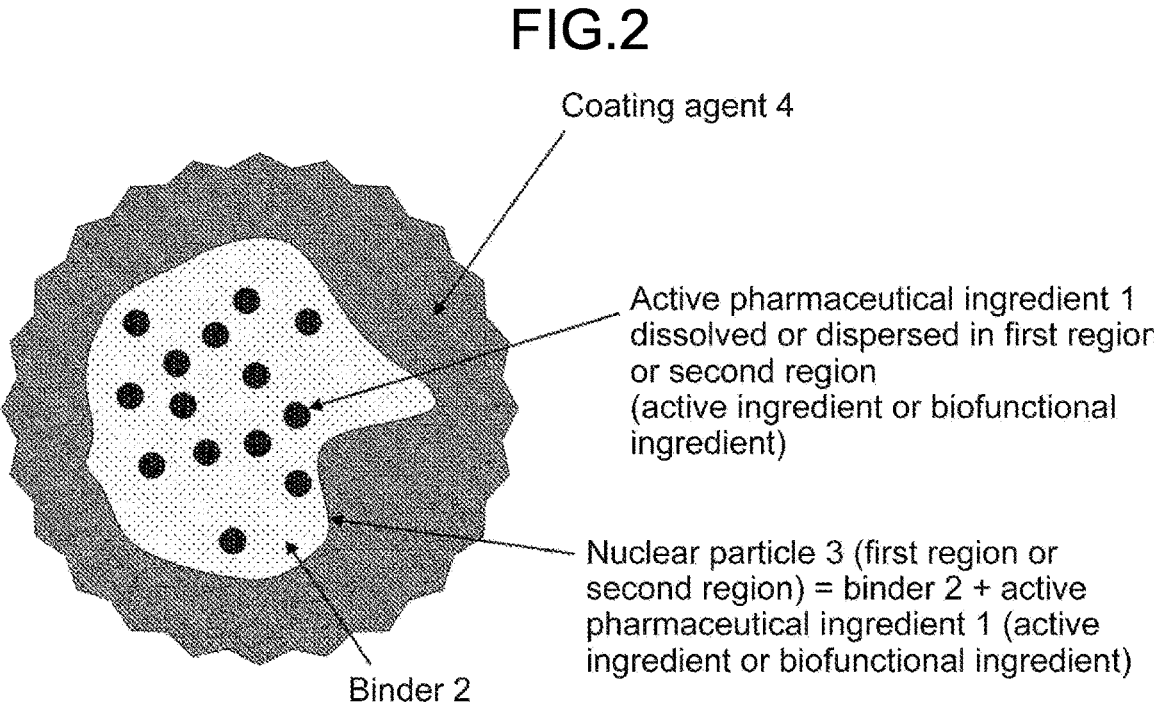

Coating agent 4

Active pharmaceutical ingredient 1
dissolved or dispersed in first region
or second region
(active ingredient or biofunctional
ingredient)

Nuclear particle 3 (first region or
second region) = binder 2 + active
pharmaceutical ingredient 1 (active
ingredient or biofunctional ingredient)

Binder 2

Second region

Inert excipient

First region

Enlargement

Corn starch dispersed in the body of granulated product

Dissolution control layer
(which is not limited to
single layer)

Active pharmaceutical
ingredient layer
(layer thickness varies
depending on regions)

Inert nuclear particle

Inert nuclear
particle

Active pharmaceutical
ingredient layer

Inert excipient

Active
pharmaceutical
ingredient layer

Inert excipient

Inert nuclear
particle

Active
pharmaceutical
ingredient layer

TABLET AND METHOD FOR PRODUCING TABLET

TECHNICAL FIELD

The present invention relates to a tablet and a method for producing the tablet, and particularly relates to a tablet capable of stably controlling an amount of an effective ingredient to be contained without spending an enormous production cost for producing the same, and a method for producing such a tablet.

BACKGROUND ART

Up to now, when granules including an active pharmaceutical ingredient are compressed to produce tablets, it is common to employ granules in which the outer surface of inert nuclear particles as an excipient is coated with an active pharmaceutical ingredient and further coated with a dissolution control layer thereon as granules for compression (for example, see FIG. 8).

PRIOR ART DOCUMENTS

Patent Document

Patent Document 1: JP 2017-210415 A
Patent Document 2: JP 2019-73459 A
Patent Document 3: JP 2019-182856 A

Non Patent Document

Non Patent Document 1: Yasushi Ochiai, "Smart Particle Design for Advanced Functional Formulations~Creation and Evaluation of Opusgran®~", Powder Technology Required for Creation of Advanced Materials 2018, [online], The Micromeritics No. 61 (2018) 28-34 <https://www.jstage.jst.go.jp/article/micromeritics/61/0/61_2018008/_pdf/-char/ja>

SUMMARY OF INVENTION

Technical Problem

The granules in which the outer surface of nuclear particles is coated with an active pharmaceutical ingredient as in the above conventional technique cause the thickness of the coating layer to be not uniform when coating the outer surface with the active pharmaceutical ingredient as long as the outer surface of nuclear particles to be the base is not close to smooth true spherical (for example, the condition as shown in FIG. 5). In the tablets obtained by compressing granules produced using nuclear particles having such a distorted outer surface (for example, the condition as shown in FIG. 6), an active pharmaceutical ingredient amount retained by respective granules depends on the surface shape of an individual nuclear particle. Thus, when tablets are compressed using granular particles having unstable active pharmaceutical ingredient amounts retained by an individual granular particle, it was difficult to strictly control the amount of an active pharmaceutical ingredient included in these tablets.

The above issue can be solved when the shape of nuclear particles coated with an active pharmaceutical ingredient can be made to be a shape similar to true spherical whereby the active pharmaceutical ingredient amount forming a coating layer can be stabilized. However, as described in Non Patent Document 1, when manufacturing granules in which the outer surface of nuclear particles is coated with an active pharmaceutical ingredient as in the above conventional technique, a versatile and simple production technique capable of providing the smooth and true spherical outer surface of nuclear particles to be the base has not yet been established.

Thus, when producing granules by coating the outer surface of nuclear particles with an active pharmaceutical ingredient, it is known that the stabilization of active pharmaceutical ingredient amount included in the granules requires an enormous production cost due to the difficulty in producing nuclear particles close to true spherical, which is essential to stabilize the active pharmaceutical ingredient amount included in such granules.

Patent Document 1 discloses an example of blending of granules (granulated composition) in the invention of the present application, Patent Document 2 discloses an example of a method for producing granules (granulated composition) in the invention of the present application, and Patent Document 3 discloses an example of a constitution of a granule (granulated composition) in the invention of the present application. However, it has not been confirmed that the tablets using these granules (granulated compositions) can stably control the amount of an effective ingredient to be contained therein and exert a masking action.

The present invention aims to provide a tablet capable of stably controlling an amount of an effective ingredient to be contained without spending an enormous production cost and a method for producing such a tablet.

Solution to Problem

As a result of intensive research to achieve the above purpose, the present inventors accomplished the present invention by the findings of a production technique which enables a stable dissolution control of an effective ingredient without spending an enormous production cost for producing the same.

That is, the present invention is as follows.

(1) A tablet obtained by compressing a mixture including at least a granulated composition including an active ingredient or biofunctional ingredient,
wherein the tablet comprises
a first region consisting of a binder including an active ingredient or biofunctional ingredient, and
a second region adjacent to the first region and consisting of the binder including the active ingredient or biofunctional ingredient,
wherein the active ingredient or biofunctional ingredient included in the first region and the second region is dispersed or dissolved without forming a layer in the binder in which each of the active ingredient or the biofunctional ingredient is included.

(2) The tablet according to (1), wherein the binder consists of an inert substance.

(3) The tablet according to (2), wherein the inert substance is at least any of glycerin fatty acid ester, gelatin, carrageenan, agar, polyethylene glycol, methyl cellulose, hydroxypropyl methylcellulose, hydroxypropyl cellulose, methacrylate copolymer, aminoalkyl methacrylate copolymer, ammonio alkyl methacrylate copolymer, ethyl acrylate-methyl methacrylate copolymer, hypromellose phthalate, hypromellose acetate succinate, cellulose acetate phthalate and polyvinyl acetate phthalate, and hardened oil or surfactant having a melting point of 80° C. or less.

(4) The tablet according to claim 1 further comprising a coating layer which coats an outer surface of each of the first region and the second region and is composed of a substance insoluble in the binder, and
wherein the first region and the second region are adjacent to each other via the coating layer.

(5) The tablet according to (4), wherein a developed interfacial area ratio Sdr between the outer surface of each of the first region and the second region and the coating layer is 100 to 700.

(6) The tablet according to (4), wherein the coating layer is composed of coating particles having an aspect ratio of 10 or less.

(7) The tablet according to (1), wherein when the binder is a masking agent for masking a predetermined characteristic of the active ingredient or biofunctional ingredient, at least a part of the active ingredient or biofunctional ingredient is included in a state of amorphous in the masking agent.

(8) The tablet according to (7), wherein the active ingredient or biofunctional ingredient is melted in the masking agent in an amount which is equal to or less than a solubility of the active ingredient or biofunctional ingredient in the masking agent.

(9) The tablet according to (7), wherein the active ingredient or biofunctional ingredient is a bitter taste compound, and the masking agent is a bitter taste inhibitor for inhibiting the bitter taste of the bitter taste compound.

(10) The tablet according to (9), wherein the bitter taste inhibitor is a glycerin fatty acid ester.

(11) The tablet according to (10), wherein the glycerin fatty acid ester is an organic acid ester.

(12) The tablet according to (11), wherein the organic acid ester is an organic acid monoglyceride.

(13) The tablet according to (12), wherein the organic acid monoglyceride is one or two or more selected from succinylated monoglycerides, citric acid esters of monoglycerides, tartaric acid esters of monoglycerides, and acetic acid esters of monoglycerides.

(14) The tablet according to (9), wherein the bitter taste compound is pharmacologically acceptable citric acid salts or succinic acid salts of the active ingredient or biofunctional ingredient.

(15) The tablet according to (6), wherein the coating particle is Japanese Pharmacopoeia corn starch.

(16) A method for producing a tablet comprising;
mixing a plurality of granulated compositions which have a first ingredient being an active ingredient or biofunctional ingredient and a binder including the first ingredient, with other substances to be mixed, and
compressing a mixture obtained by the mixing,
wherein, in each of the plurality of the granulated compositions to be compressed, the first ingredient is dispersed or dissolved without forming a layer in the binder.

(17) The method according to (16), wherein the binder consists of an inert substance.

(18) The method according to (17), wherein the inert substance is at least any of glycerin fatty acid ester, gelatin, carrageenan, agar, polyethylene glycol, methyl cellulose, hydroxypropyl methylcellulose, hydroxypropyl cellulose, methacrylate copolymer, aminoalkyl methacrylate copolymer, ammonio alkyl methacrylate copolymer, ethyl acrylate-methyl methacrylate copolymer, hypromellose phthalate, hypromellose acetate succinate, cellulose acetate phthalate and polyvinyl acetate phthalate, and hardened oil or surfactant having a melting point of 80° C. or less.

(19) The method according to (16), wherein each of the plurality of the granulated compositions to be compressed further has a coating layer which coats an outer surface of the binder including the first ingredient and is composed of a substance insoluble in the binder.

(20) The method according to (16), wherein when the binder is a masking agent for masking a predetermined characteristic of the active ingredient or biofunctional ingredient, at least a part of the active ingredient or biofunctional ingredient is included in a state of amorphous in the masking agent.

Advantageous Effects of Invention

The tablet and the production method thereof according to the present invention can provide a tablet capable of stably controlling an amount of an effective ingredient to be contained without spending an enormous production cost for producing the same, and a method for producing such a tablet.

BRIEF DESCRIPTION OF DRAWINGS

FIG. 1 is an image diagram of a cross-section structure of the tablet obtained by tableting (compressing) a mixture obtained by homogeneously mixing the granulated composition according to the present invention, an excipient, a disintegrant, a tablet binder, a lubricant and the like. In the first region or the second region, an active pharmaceutical ingredient is dissolved or dispersed without forming a coating layer (the amount of an active pharmaceutical ingredient included in an individual granular particle is easily controlled to be constant).

FIG. 2 is an image diagram of a cross-section structure of an individual granulated composition included in the tablet according to the present invention.

DESCRIPTION OF EMBODIMENTS

Figure 3:
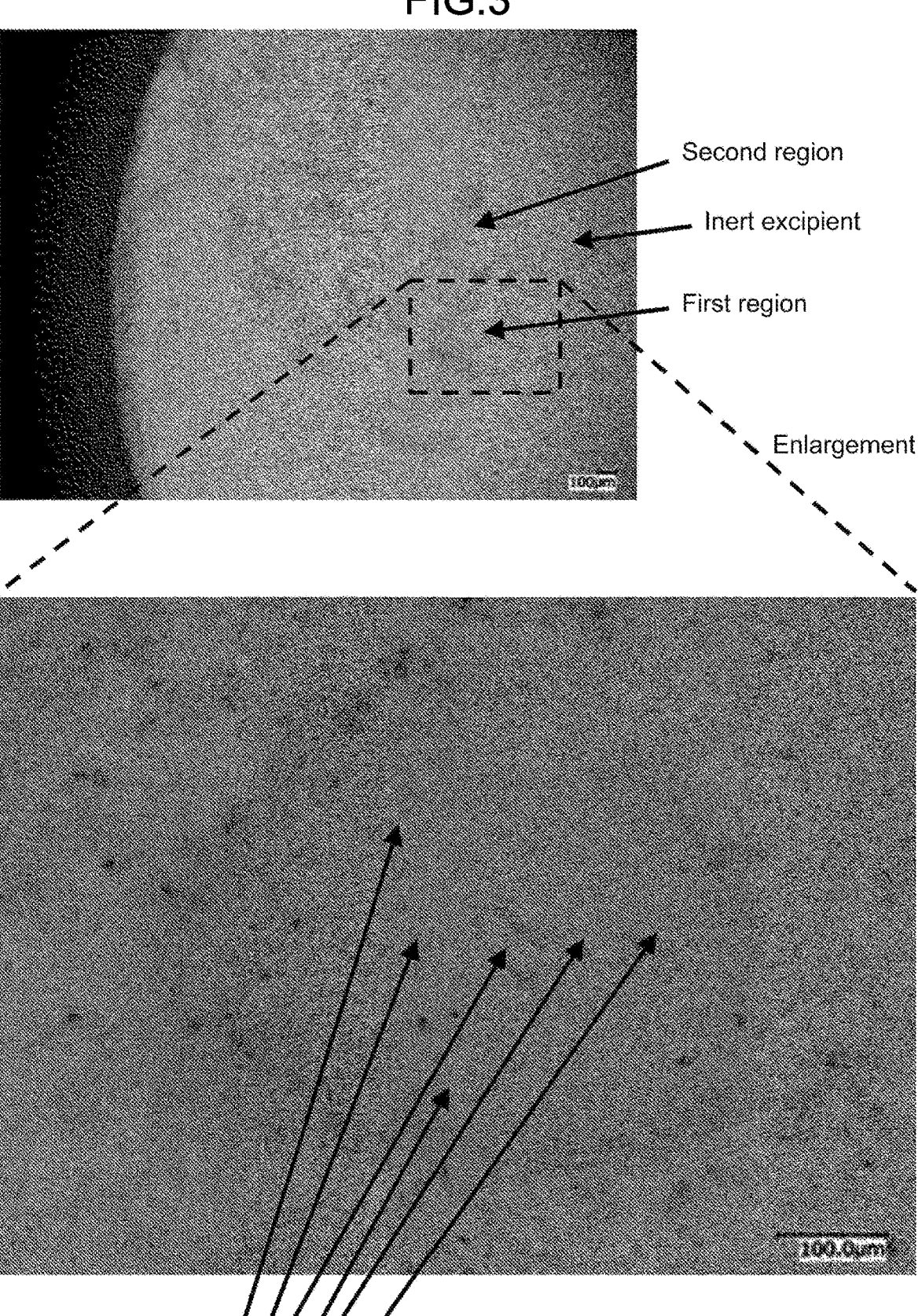
FIG. 3 is a photograph of the cross-section of the tablet actually manufactured in Example 1, which is schematically shown in FIG. 1.

The present invention is described in detail below.

The tablet according to the present invention is produced by compressing a granulated composition including an active ingredient or biofunctional ingredient. Hereinafter, the granulated composition used for compressing the tablet according to the present invention and a method for producing the tablet using thereof are described.

The granulated composition according to the present invention includes nuclear particles, and the nuclear particles include at least an active ingredient or biofunctional ingredient and a binder. The active ingredient or biofunctional ingredient in the granulated composition according to the present invention is contained in the binder and/or inclusion particles to be included in the nuclear particle as needed. Moreover, the granulated composition according to the present invention can also have a constitution in which coating particles are attached around the nuclear particles.

FIG. 2 is an image diagram of a cross-section structure of an individual granulated composition included in the tablet according to the present invention. The granulated composition included in the tablet according to the present invention is described using FIG. 2 below.

The granulated composition according to the present invention has a region composed of a binder and an active ingredient or biofunctional ingredient included in the binder (equivalent to the first region or second region) as a nuclear particle.

As shown in FIG. 2, in the nuclear particle as an embodiment of the present invention, particulate active ingredients or biofunctional ingredients (equivalent to inclusion particles) are mixed to be dispersed in the binder.

The binder constituting the nuclear particle according to the present invention consists of an inert substance. Specifically, for example, at least any of gelatin, carrageenan, agar, polyethylene glycol, methyl cellulose, hydroxypropyl methylcellulose, hydroxypropyl cellulose, a methacrylate copolymer, an aminoalkyl methacrylate copolymer, an ammonio alkyl methacrylate copolymer, an ethyl acrylate-methyl methacrylate copolymer, hypromellose phthalate, hypromellose acetate succinate, cellulose acetate phthalate and polyvinyl acetate phthalate, and a hardened oil or a surfactant having a melting point of 80° C. or less can be employed as the above inert substance.

The outer surface of the nuclear particle consisting of the above particulate active ingredients or biofunctional ingredients and the binder is coated with coating particles composed of a substance insoluble in the binder (coating layer).

Specifically, the above coating particles are composed of coating particles having an aspect ratio of 10 or less. The employable coating particles are one or two or more of powders selected from ethyl cellulose, corn starch, rice starch, wheat starch, potato starch, calcium stearate, magnesium carbonate, low substituted sodium carboxymethyl starch, sodium starch glycolate, anhydrous silicic acid, magnesium silicate, diatomaceous earth, bentonite, zeolite, silicon dioxide, powdered agar, croscarmellose sodium, crospovidone, and talc.

The above active ingredient or biofunctional ingredient (a first ingredient) is not particularly limited and can be any ingredient dispersible or dissolvable in the binder described below.

Examples of the active ingredient may include chlorpromazine, thioridazine, olanzapine, quetiapine, risperidone, haloperidol, perphenazine, aripiprazole, paliperidone, amoxapine, fluoxetine, fluvoxamine, paroxetine, sertraline, trazodone, nefazodone, clomipramine, desipramine, nortriptyline, levodopa, donepezil, bromocriptine, pergolide, pramipexole, ropinirole, methylphenidate, atomoxetine, pregabalin, lacosamide, carbamazepine, clonazepam, levetiracetam, oxcarbazepine, phenobarbital, phenytoin, topiramate, valproic acid, divalproex sodium, zonisamide, alprazolama, lorazepam, oxazepam, clorazepate, diazepam, halazepam, zolpidem, phenobarbital, ethchlorvynol, glutethimide, pentobarbital, sildenafil, tadalafil, cyclosporin, mycophenolate mofetil, sirolimus, tacrolimus, terazosin hydrochloride, benazepril, captopril, clonidine hydrochloride, enalapril, hydralazine hydrochloride, losartan potassium, methyldopate hydrochloride, minoxidil, moexipril, candesartan, irbesartan, losartan, telmisartan, valsartan, guanabenz acetate, guanadrel sulfate, guanfacine hydrochloride, reserpine, atenolol, betaxolol, bisoprolol, carteolol, carvedilol, labetalol, metoprolol, pindolol, propranolol, sotalol, timolol, amlodipine, diltiazem, nicardipine, nifedipine, nisoldipine, verapamil, fenofibrate, atorvastatin, fluvastatin, lovastatin, pravastatin, simvastatin, mosapride, itopride, domperidone, trimebutine, metoclopramide, bisacodyl, diphenoxylate hydrochloride, loperamide, clopidogrel bisulfate, phytonadione, ticlopidine, sodium warfarin, limaprost, beraprost, almotriptan, ergotamine, frovatriptan, methysergide, sumatriptan, zolmitriptan, azathioprine, hydroxychloroquine, leflunomide, methotrexate, penicillamine, sulfasalazine, acetaminophen, aspirin, diclofenac, fenoprofen, ibuprofen, ketoprofen, naproxen, indometacin, meloxicam, piroxicam, celecoxib, rofecoxib, codeine, fentanyl, hydrocodone, hydromorphone, levorphanol, meperidine, morphine, oxycodone, pentazocine, propoxyphene, tramadol, tapentadol imatinib, erlotinib, sunitinib, sorafenib, lapatinib, gefitinib, dasatinib, lenalidomide, clofazimine, cycloserine, ethionamide, rifabutin, albendazol, ivermectin, mebendazole, praziquantel, valaciclovir, valganciclovir, indinavir, lamibudine, nelfinavir mesylate, nevirapine, ritonavir, oseltamivir, amoxicillin, amoxicillin cefuroxime sodium, cefuroxime axetil, penicillin, cefixime, erythromycin, ciprofloxacin, methotrexate, mercaptopurine, digoxin, disopyramide, flecainide acetate, mexiletine hydrochloride, moricizine hydrochloride, procainamide hydrochloride, propafenone hydrochloride, quinidine, sotalol hydrochloride, tocainide, lansoprazole, omeprazole, pantoprazole, rabeprazole, sucralfate, acarbose, metformin, nateglinide, repaglinide, acetohexamide, chlorpropamide, tolazamide, tolbutamide, glimepiride, glipizide, glyburide, pioglitazone, rosiglitazone, amiloride hydrochloride, bumetanide, ethacrynic acid, furosemide, torasemide, hydrochlorothiazide, chlortalidone, indapamide, metolazone, polythiazide, quinethazone, trichlormethiazide, spironolactone, triamteren, allopurinol, colchicine, probenecid, sulfinpyrazone, albuterol sulfate, montelukast sodium, theophylline, zileuton, azatadine, chlorpheniramine maleate, diphenhydramine hydrochloride, clemastine, fexofenadine, hydroxyzine, loratadine, desloratadine, and pharmacologically acceptable salts thereof.

The biofunctional ingredient is absorbed in the body, provides a predetermined action on the body and used for a functional food such as supplements. Examples of the biofunctional ingredient may include coenzyme Q10, lutein, curcuminoid, silymarin, astaxanthin, zeaxanthin, cryptoxanthin, fucoxanthin, lycopene, sesamin, α-lipoic acid, fatsoluble vitamins (vitamin A, vitamin D, vitamin E, vitamin K) and derivatives thereof, docosahexaenoic acid (DHA), eicosapentaenoic acid (EPA), a saw palmetto extract (oleic acid, lauric acid, myristic acid, linoleic acid, palmitic acid), St. John's wort (hypericin), royal jelly (decenoic acid), hesperidin, nobiletin, quercetin, kaempferol, myricitrin, catechin, daidzein, glycitein, genistein, myricetin, stilbene, and usable derivatives thereof.

The active ingredient or biofunctional ingredient in the description of the present application is not limited to the above examples, and any ingredients can be used as long as they are applicable to the granulated composition of the present invention. Moreover, the active ingredient or biofunctional ingredient in the description of the present application can be aqueous or non-aqueous. Here, for example, when a bitter taste ingredient is used as the active ingredient or biofunctional ingredient in the description of the present application, employable examples include, but are not limited to, a polyphenol and B-complex vitamins.

Moreover, the granulated composition according to the present invention can also have a constitution in which a masking agent masks a predetermined characteristic of a predetermined compound to be masked. When a tablet is compressed using such a masked granulated composition, the tablet in which the predetermined characteristic of the predetermined compound is masked can be provided.

As a result of intensive research, the present inventors found that, when masking a predetermined compound, effective masking of the predetermined compound can be achieved by forming particulate nuclear particles so that at least a part of the above predetermined compound is included in a state of amorphous in a masking agent having a masking function on the predetermined compound.

The granulated composition obtained by masking a predetermined compound to be masked using a masking agent is described in detail below. Here, a case where the predetermined characteristic to be masked is "bitterness" is described as an example.

Polyphenols as the bitter taste ingredients are not particularly limited as long as it is generally orally ingestible, and examples of polyphenols include catechins [non-polymeric catechins (epimer catechins such as epicatechin, epigallocatechin, epicatechin gallate, and epigallocatechin gallate, non-epimer catechins such as catechin, gallocatechin, catechin gallate, and gallocatechin gallate), polymeric catechins], theaflavins, thearubigins, tannin, soybean isoflavone, enzyme-treated rutin, flavangenol, a *Myrica rubra* extract, enzyme-treated isoquercetin, pycnogenol, xanthohumol, hop flavonoid, a hop extract, proanthocyanidin (grape seed polyphenol), luteolin, strictinin, pelargonidin, apigenin, diosmin, hesperetin, naringin, phloretin, kenphenol, myricetin, corilagin, chlorogenic acid, anthocyanin, a quercetin glycoside, a phloretin glycoside, isoprenoid, phytic acid, genistein, daidzein, and guava leaf polyphenol.

Examples of the bitter taste ingredient other than the polyphenols include peptides (peptides consisting of 2 to 4 amino acids having at least 1 branched chain amino acid such as leucine, isoleucine, and valine), caffeines (a caffeine extract), kale, quinine, a cinchona (bark) extract, a phellodendron extract, dandelion, *Swertia japonica* (a *Swertia japonica* extract), *Picrasma quassioides* (a *Picrasma quassioides* extract), guarana, absinthin, Genthio-oligosaccharide, and minerals (magnesium salts such as magnesium sulfate and magnesium chloride, and calcium salts such as calcium sulfate.)

Examples of such a bitter taste ingredient include an azithromycin hydrate, aspirin and dialuminate, acetaminophen, atenolol, atovaquone, atomoxetine hydrochloride, an atorvastatin calcium hydrate, amiodarone hydrochloride, meglumine sodium amidotrizoate, ethyl aminobenzoate, amlodipine besilate, an amoxicillin hydrate, aripiprazole, alimemazine tartrate, sodium alginate, albendazol, an ampicillin hydrate, ambroxol hydrochloride, isosorbide, itraconazole, ibuprofen, irbesartan, indometacin, an ecabet sodium hydrate, ethambutol hydrochloride, ethosuximide, ebastine, epinastine hydrochloride, epinephrine hydrochloride, epirizole, ephedrine hydrochloride, an entecavir hydrate, an oxycodone hydrochloride hydrate, oseltamivir phosphate, olanzapine, olmesartan medoxomil, olopatadine hydrochloride, ondansetron, galantamine hydrobromide, a calciferol combination drug, carteolol hydrochloride, carbocisteine, candesartan cilexetil, quetiapine fumarate, granisetron hydrochloride, potassium clavulanate, clarithromycin, glimepiride, clemastine fumarate, a clocapramine hydrochloride hydrate, chlorpheniramine maleate, ketotifen fumarate, ketoprofen, solifenacin succinate, colistin sodium methanesulfonate, salbutamol sulfate, sarpogrelate hydrochloride, diclofenac sodium, a sitafloxacin hydrate, dihydrocodeine phosphate, diphenhydramine hydrochloride, diphenhydramine salicylate-diprophylline, a dibucaine hydrochloride combination drug, a cyproheptadine hydrochloride hydrate, dimemorfan phosphate, sildenafil citrate, cilostazol, silodosin, simvastatin, stiripentol, sumatriptan succinate, a sultamicillin tosilate hydrate, sulpyrine, cetirizine hydrochloride, a cetylpyridinium combination drug, cetraxate hydrochloride, cefalexin, a cefcapene pivoxil hydrochloride hydrate, cefditoren pivoxil, cefdinir, cefteram pivoxil, cefpodoxime proxetil, selegiline hydrochloride, zonisamide, zolpidem tartrate, zolmitriptan, tamsulosin hydrochloride, a taltirelin hydrate, tiaramide hydrochloride, tipepidine hibenzate, theophylline, dextromethorphan hydrobromide, dexamethasone, tebipenem pivoxil, telmisartan, docarpamine, doxazosin mesilate, a tosufloxacin tosilate hydrate, donepezil hydrochloride, tramadol hydrochloride, triazolam, triamcinolone acetonide, a trimetoquinol hydrochloride hydrate, droxidopa, troxipide, domperidone, naftopidil, naproxen, nalidixic acid, nifedipine, valacyclovir hydrochloride, valsartan, sodium valproate, a paroxetine hydrochloride hydrate, pioglitazone hydrochloride, bicalutamide, a sodium picosulfate hydrate, hydroxyzine pamoate, hydrochlorothiazide, pipamperone hydrochloride, pyrantel pamoate, famotidine, a faropenem sodium hydrate, phenacetin, phenylbutazone, phenobarbital, pranoprofen, pravastatin sodium, flecainide acetate, pregabalin, brotizolam, procaterol hydrochloride, propranolol hydrochloride, bepotastine besilate, benzalkonium chloride, a benzylpenicillin benzathine hydrate, benzbromarone, benzethonium chloride, pentazocine, pentoxyverine citrate, a fosfomycin calcium hydrate, a bosentan hydrate, polaprezinc, polycarbophil calcium, calcium polystyrene sulfonate, miglitol, mycophenolate mofetil, mizoribine, a mitiglinide calcium hydrate, mequitazine, methylephedrine hydrochloride, metoclopramide, metronidazole, mefenamic acid, mebendazole, memantine hydrochloride, meloxicam, a mosapride citrate hydrate, lafutidine, ramosetron hydrochloride, lamotrigine, lansoprazole, rizatriptan benzoate, risperidone, ritonavir, a rilmazafone hydrochloride hydrate, levetiracetam, levocetirizine hydrochloride, a levofloxacin hydrate, roxatidine acetate hydrochloride, rosuvastatin calcium, lopinavir, ropinirole hydrochloride, and loratadine.

As the above coating particles, known coating particles for pharmaceuticals, functional foods and the like can be used as long as the particles are acceptable by the body, particularly pharmaceutically or food hygienically acceptable, and insoluble in the above binder. Examples may include ethyl cellulose, corn starch, rice starch, wheat starch, potato starch, calcium stearate, magnesium carbonate, low substituted sodium carboxymethyl starch, sodium starch glycolate, anhydrous silicic acid, magnesium silicate, diatomaceous earth, bentonite, zeolite, silicon dioxide, powdered agar, croscarmellose sodium, crospovidone, and talc, and a mixture of one or two or more of these can be used.

The particle diameter of these coating particles is not particularly limited but preferably d50=5 to 70 μm, and particularly preferably d50=10 to 30 μm. When a particle diameter is too large, the adhesiveness to the above nuclear particles is inferior and the water absorbency may also be insufficient, whereas when a particle diameter is too small, the coating particles are likely to scatter when forming a fluidized bed during the granulation operation. Moreover, the particle diameter of the coating particles may impact the Sdr value described below, and it is thus preferable to consider the particle diameter so that an Sdr value can be within the range defined in the present invention. Further, the coating particles preferably have an angle of repose of 60° or less, and particularly preferably 50° or less, but not particularly limited thereto. The fluidity of the thus obtained granulated composition is improved, enabling the workability and the productivity in the subsequent step such as a step of compressing a granulated composition and the like to be more improved.

Further, the coating particles preferably have, but are not particularly limited to, an aspect ratio of 11 or less, and particularly preferably 4 or less. When the coating particles have an aspect ratio of more than 11, the Sdr value described below becomes large and the Sdr value of the obtained granulated composition is likely to vary widely, and thus the Sdr value of the present invention may not be stably accomplished. This point will be described below. As a simple way of determining an aspect ratio of the coating particles, an aspect ratio of the coating particles can be easily determined as a major axis/minor axis ratio of the microscope-imaged particles randomly selected from the images taken. This image can be obtained by homogeneously suspending the coating particles in, for example, an inert fluid such as a silicone oil, then enclosing the particles in a slide glass and taking an image using a microscope.

As the binder, a known binder used for the granulation operation can be used as long as it is pharmaceutically or food hygienically acceptable and capable of retaining a granular figure by binding the above inclusion particles with each other and the inclusion particles with the above coating particles, or it is a polymer which controls the dissolution property of the active ingredient or biofunctional ingredient. Specifically, examples may include glycerin fatty acid ester, gelatin, carrageenan, methyl cellulose, hydroxypropyl methylcellulose, hydroxypropyl cellulose, methacrylate copolymer, hypromellose phthalate, hypromellose acetate succinate, cellulose acetate phthalate, and polyvinyl acetate phthalate, and one or two or more of these polymeric substances dissolved in a solvent such as water or ethanol can be used as the above binder. Examples of the solvent other than water may include, in addition to ethanol, acetic acid, acetone, t-butyl methyl ether, ethyl acetate, 2-propanol, methanol, ammonia, hexane, pyridine, and dichloromethane.

The glycerin fatty acid ester as the masking agent including a bitter taste inhibitor is desirably, for example, an organic acid ester. Further, the organic acid ester as the masking agent including a bitter taste inhibitor is preferably, for example, an organic acid esters of monoglycerides.

Here, the organic acid monoglyceride as the masking agent including a bitter taste inhibitor can be one or two or more selected from succinylated monoglycerides, citric acid esters of monoglycerides, tartaric acid esters of monoglycerides, and acetic acid esters of monoglycerides.

Next, the above inclusion particles form the nuclear particle together with the above binder to be the core of the nuclear particle. The presence of this inclusion particle enables good retention of the nuclear particle figure even when the binder has a weak and tenuous gel strength. As long as the above active ingredient and/or biofunctional ingredient can be present in the particle figure in the binder, it can be used as an inclusion particle. Moreover, the inclusion particle can be blended separately from the active ingredient and biofunctional ingredient, and the inclusion particle in this case can be a pharmaceutically or food hygienically acceptable compound, and examples thereof include the same as compounds shown as the above coating particles.

Additionally, compounds capable of retaining the granular figure can be reasonably used as the above inclusion particle in place of the polymeric substances having a gelling action. Compounds convertible from liquid to solid in a temperature-dependent manner can be the inclusion particle. The compounds applicable thereto include compounds that become a liquid state and flow when heated although the compounds are solid at normal temperature. The compounds applicable thereto include a resin having a softening temperature ranging from 50° C. to 200° C. and an oil and a fat and a surfactant having a melting point of 80° C. or less. Specifically, examples of the resin may include low density polyethylene, a microcrystalline wax, paraffin, and shellac, and examples of the fats and oils may include a hydrogenated hardened oil, beeswax, rice bran wax, stearyl alcohol, and behenyl alcohol, and examples of the surfactant may include polyglycerin fatty acid ester, monoglyceryl stearate, monoglyceryl behenate, polyethylene glycol 4000, polyethylene glycol 6000, polyethylene glycol 20000, polyoxyethylene-added polyglycerin fatty acid ester, and polyoxyethylene and/or polyoxypropylene-added glycol.

The granulated composition of the present invention, as described above, is the composition comprising the active ingredient or biofunctional ingredient which is contained in the inclusion particle and/or the binder forming the above-described nuclear particle. The form thereof encompasses 3 types of forms shown in, for example, FIGS. 1 to 3 of Patent Document 3.

The granulated composition of the present invention, as shown in FIG. 2, has coating particles 4 attached around the nuclear particle 3. In this case, because the coating particles 4 are insoluble in the binder 2 as described above, the coating particles 4 attach to the nuclear particle 3 while maintaining the form thereof without their surfaces being dissolved. Thus, there is a definite interface between the nuclear particle 3 and the coating particles 4. Moreover, the coating particles 4 coat the surface of the nuclear particle 3, and the width and depth of the gap between the coating particles depend on the shape and size of the coating particles. In other words, the surface roughness of the granulated composition of the present invention is determined according to the shape and size of the coating particles. Meanwhile, the method for evaluating the waviness, roughness, small unevenness of the object surface is specified in International Standard "ISO 25178 Surface texture (surface roughness measurement)." Among those evaluation methods, the "developed interfacial area ratio Sdr" refers to numerical conversion expressed in the percentage form (%) showing a degree in the increase of a surface area developed smoothly when unevenness identified in a specific area (for example, 50 μm square) is spread out in comparison with a perfect smooth surface in the case of no unevenness being present in the same area. The developed interfacial area ratio Sdr can be measured by obtaining a three-dimensional information of waviness, roughness, and small unevenness of the object surface from interference fringes obtained by using a white-light interference microscope when a lens moves in the Z-direction while irradiating the surface of the object with a white light.

Here, when the surface roughness of the granulated product affects the slip property and the easiness in intertwinement and further causes segregation, there is a correlation between the degree of segregation and the developed interfacial area ratio Sdr. Further, as the surface roughness of the granulated product is determined by the shape and size of the coating particles, the segregation of the granulated product can be certainly prevented by selecting suitable coating particles and the developed interfacial area ratio Sdr in the granulated composition of the present invention.

Thus, in the granulated composition of the present invention, this developed interfacial area ratio Sdr is 100 to 700, and preferably 150 to 400. When the Sdr is too large, the binding property and the easiness in intertwinement of granulated products are too strong and segregation may be caused at the time of mixing the above nuclear particle and other excipients and the active ingredient or biofunctional ingredient. On the other hand, when the Sdr is too small, particles slip each other to the extent that a homogeneously dispersed state cannot be maintained in the mixing operation thereby also likely causing segregation.

The developed interfacial area ratio Sdr in the granulated composition of the present invention is significantly affected by the size and shape of the above coating particles as described above, and the adjustment of the size and shape of the coating particles enables the stable achievement of the above Sdr value. Specifically, adjusting the particle diameter and aspect ratio of the coating particles so as to be within the range as described above easily enables the stable achievement of the above Sdr value. In this case, the shape of coating particles together with the size thereof significantly affects the Sdr value. For example, as in Comparative Example 1 described below, when columnar or needle-like coating particles having an aspect ratio more than the preferable range described above are used, Sdr values of the obtained granulated particles not only become large but also vary widely. Thus, it is likely to be difficult to stably achieve the above Sdr value. The granulated composition in the invention of the present application only needs to achieve the developed interfacial area ratio Sdr of the above range and is not limited by the size (particle diameter) or shape (aspect ratio) of the coating particles.

Suitable and employable method for obtaining the granulated composition in such a form according to the present invention comprises dissolving or dispersing the above binder and the above active ingredient or biofunctional ingredient (in a state of being dispersed or dissolved in a hydrophobic liquid as needed) in water or other solvents, further separately blending the above inclusion particles as needed to prepare a solution for granulation, dripping the solution for granulation to a fluidized bed through which the above coating particles flow, and letting the coating particles absorb water and other solvents by attaching the above coating particles to the droplet surface, thereby granulating the composition into granular.

In this case, according to the granulated composition of the present invention, a concentration of the above polymeric substance constituting the above binder can be set low when preparing the above solution for granulation. Thus, even when a solution for granulation has a low gel strength with a low concentration of a gelling agent (polymeric substance), the droplets become the nuclear particle capable of retaining the particulate figure in the above fluidized bed due to the presence of the above inclusion particles, whereby a good granulated product around which the above coating particles attach can be obtained.

In the granulated composition of the present invention, known additives can be suitably blended within a scope not deviating from the purpose of the present invention. For example, sweeteners, coloring agents, preservatives, thickeners, stabilizers, antioxidants, flavoring agents, acidulants, seasonings, and pH adjusters can be blended in the above nuclear particle as needed.

Subsequently, the method for producing a tablet by compressing the granulated composition according to the present invention is described.

The tablet of the present invention can be produced by compressing a mixture including, for example, the above granulated composition, an excipient, a disintegrant, a tablet binder, and a lubricant.

Examples of excipient are not particularly limited, and may include crystalline cellulose, lactose, dextrin, glucose, sugar alcohol, hydroxypropyl cellulose, processed starch, indigestible dextrin, and indigestible starch, and one or two or more of these can be preferably used.

Examples of disintegrant are not particularly limited, and may include agar, carboxymethylcellulose calcium, carboxymethylcellulose sodium, and starch, of which one or two or more can be preferably used.

Examples of tablet binder are not particularly limited, and may include gum arabic, gelatin, sodium alginate, methyl cellulose, hydroxypropyl cellulose, hydroxypropyl methylcellulose, starch, processed starch, carboxymethyl cellulose, polyvinylpyrrolidone, and polyvinyl alcohol, and one or two or more of these can be preferably used.

Examples of lubricant are not particularly limited, and may include calcium stearate, magnesium stearate, sucrose fatty acid ester, fine-grain silicon dioxide, talc, a hydrogenated plant oil, macrogol, and a silicone oil, and one or two or more of these can be preferably used.

In the tablet of the present invention, known additives can be suitably blended within a scope not deviating from the purpose of the present invention and, for example, single or a mixture of excipients, disintegrants, tablet binders, lubricants, sweeteners, flavoring agents, and coloring agents can be blended in the above tablet as needed.

The mixture obtained by homogenously mixing the granulated composition, excipients, disintegrants, tablet binders, lubricants and the like as described above is compressed using a rotary continuous tablet press machine or an eccentric tablet press machine, whereby the tablet according to the present invention is produced.

FIG. 1 is an image diagram of a cross-section structure of the tablet obtained by tableting (compressing) a mixture obtained by homogeneously mixing the granulated composition according to the present invention, excipients, disintegrants, tablet binders, lubricants and the like (other substances to be mixed). Namely, the tablet according to the present invention can be produced by mixing a plurality of granulated compositions having a first ingredient being an active ingredient or biofunctional ingredient and a binder including the first ingredient, and other substances to be mixed, and compressing thus obtained mixture.

When the granulated composition of the present invention and the mixture obtained by homogenously mixing excipients, disintegrants, tablet binders, lubricants and the like are compressed, the tablet as shown in FIG. 1 is obtained.

In the tablet according to the present invention, as shown in FIG. 1, a plurality of the granulated compositions according to the present invention are homogeneously dispersed, and in such a tablet, these granulated compositions are adjacent to each other via an inert excipient.

At this time, the adjacent two granulated compositions have the nuclear particles consisting of the active ingredient or biofunctional ingredient and the binder respectively. One of the nuclear particles is equivalent to a "first region", whereas the other is equivalent to a "second region."

In the positional relation between the two adjacent granulated compositions, not only a state in which the inert excipient intervene between the two adjacent granulated compositions but also a state in which both compositions are in contact without an intervention by the inert excipient can be caused, however both states are included in the concept of being "adjacent."

EXAMPLES

The present invention is described in furthermore detail in reference to Examples below, but the present invention is not at all limited thereto.

Manufacture of a Granulated Composition

Example 1

The granulated composition constituting the tablet to be manufactured according to Example 1 was manufactured by the applicant of the present application based on the method below. Namely, a sol solution was prepared under a condition of 50 to 80° C. so that the granulated composition to be manufactured as a result could have, after dried, the composition shown in Table 1 (provided that corn starch was excluded), and discharged as droplets having a size of a diameter of about 0.3 mm to a rolling cooling medium (Japanese Pharmacopoeia corn starch) at room temperature (example: 23° C.). These droplets, after cooled in the cooling medium and solidified, were classified using a 140-mesh sieve. In Table 1, Corn starch 1 is contained in the nuclear particle as the "inclusion particle" as a substitute for an active ingredient or a nutritionally functional ingredient, and Corn starch 2 is to be the coating particles. In Example 1, Corn starch 1 is blended as a substitute for an active ingredient or a nutritionally functional ingredient only for the sake of understanding and evaluating the structure and function of the tablet manufactured by the formulation technique according to the present invention, however, when the granulated composition according to the present invention containing an active ingredient or a nutritionally functional ingredient is actually produced, an active ingredient or a nutritionally functional ingredient is contained in place of the above Corn starch 1.

(Manufacture of an Oral Disintegrating Tablet)

The tablet to be manufactured according to Example 1 was manufactured by the applicant of the present application based on the method below. Namely, each ingredient was weighed so that the tablet to be manufactured as a result could have the composition shown in Table 2, put and sealed in a 40 cm×70 cm clear polyethylene bag, mixed by inverting by hand for 10 minutes to prepare a mixed powder for compressing, and a round flat oral disintegrating tablet (diameter 7 mm, weight per tablet 120 mg) was produced using a rotary tablet press machine (PICCOLA D8).

TABLE 1

| Granulated composition of Example 1 | |
| --- | --- |
| | Amount of each ingredient (wt %) |
| d-α-Tocopherol | 0.3 |
| Triethyl citrate | 0.4 |
| Pig gelatin | 9.6 |
| Corn starch 1 | 7.7 |
| Corn starch 2 | 80.0 |
| Purified water | 2.0 |

TABLE 2

| Tablet composition of Example 1 | | | | | |
| --- | --- | --- | --- | --- | --- |
| Product name | Manufacturer name | Commom name | Per tablet (mg) | Feed weight (g) | Percentage (%) |
| Granulated composition of Table 1 | | | 7.5 | 7.5 | 6.25 |
| Granutol R | Freund Corporation | D-Mannitol | 80.1 | 80.1 | 66.75 |
| CEOLUS UF711 | Asahi Kasei Corporation | Crystalline cellulose | 18.0 | 18 | 15 |
| Adsolider 101 | Freund Corporation | Light anhydrous silicic acid | 1.8 | 1.8 | 1.5 |
| KICCOLATE ND-200 | Asahi Kasei Corporation | Croscarmellose Na | 6.0 | 6 | 5 |
| Kollidon CL-F | BASF | Crospovidone | 3.6 | 3.6 | 3 |
| HPC_SSL_SFP | Nippon Soda Co., Ltd. | HPC | 1.2 | 1.2 | 1 |
| Aspartame | Ajinomoto Co., Inc. | Aspartame | 0.6 | 0.6 | 0.5 |

TABLE 2-continued

| | | | Per tablet (mg) | Feed weight (g) | Percentage (%) |
|---|---|---|---|---|---|
| Product name | Manufacturer name | Commom name | | | |
| Magnesium stearate | TAIHEI CHEMICAL INDUSTRIAL CO., LTD. | Magnesium stearate | 1.2 | 1.2 | 1 |
| Total | | | 120.0 | 120 | 100 |

Tablet composition of Example 1

Stability Evaluation of an Active Pharmaceutical
Ingredient Content in the Granulated Composition
of the Present Application Example 2

The Stability evaluation of the active pharmaceutical ingredient content in the granulated composition of the present application can be carried out by evaluating the variation of the active pharmaceutical ingredient content in an individual granulated composition particle. However, the amount of the active pharmaceutical ingredient included in such a single particle is extremely small and thus it is difficult to directly measure its concentration by high performance liquid chromatography or the like. Accordingly, in Example 2, a tablet including a plurality of the granulated composition particles was produced, then the whole tablet was divided so that a plurality of such particles could appear on the torn surface. The number of images of the active pharmaceutical ingredient particles observed on such a torn surface was counted and compared among respective particles to evaluate variations. This evaluation substitutes for the stability evaluation of the active pharmaceutical ingredient content.

Evaluation Method

The internal structure of the tablet compressed by the method of Example 1 as described above can be confirmed by, for example, non-destructive three-dimensional structure observation using a 3D X-ray microscope or detailed observation by cross-section polishing using an ion milling device (TOSHIBA NANOANALYSIS CORPORATION website, "Observation of a Coating Layer on Pharmaceutical Particles" https://www.nanoanalysis.co.jp/business/case_example_223.html).

In Example 2, a digital microscope VHX-900F manufactured by KEYENCE CORPORATION was used to observe the internal structure of the tablet.

Moreover, the distribution of inorganic and organic ingredients and active pharmaceutical ingredient particles inside the tablet can be visualized and observed by Time of Flight Secondary Ion Mass Spectrometry (TOF-SIMS/cross-section analysis) (Sumika Chemical Analysis Service, Ltd. "Inner observation and chemical mapping of tablet by X-ray CT and TOF-SIMS" https://www.scas.co.jp/technical-informations/technical-news/pdf/tn369.pdf).

In Example 2, a digital microscope VHX-900F manufactured by KEYENCE CORPORATION was used to observe the internal structure of the tablet.

As shown in FIG. 1, the above active ingredient or biofunctional ingredient contained in each granulated composition which is included in the tablet dispersedly as described above is dispersed without forming a layer in the nuclear particle in which each of the active ingredient or biofunctional ingredient is included. Moreover, concentrations of the above active ingredient or biofunctional ingredient contained in the nuclear particles constituting respective granulated compositions are substantially equal between the nuclear particles by thoroughly stirring and mixing the above active ingredient or biofunctional ingredient and the binder when manufacturing the nuclear particle solution. Thus, when enough stirring time is taken for mixing, the mixing proceeds in a mixture in a state where a concentration is inhomogeneous as time goes by, and the concentration of the mixture reaches to a homogeneous state. This is known in the stirring technology as the dispersion phenomenon (Kyoto University, "Chemical Experimental Technique II (Yoshimura Yosuke), 2014 lecture handout, the 5th (May 15): Topic on mixing and dispersion" http://kuchem.kyoto-u.ac.jp/ubung/yyosuke/chemmeth/chemmeth05.pdf).

FIG. 3 is a photograph of the cross-section of the tablet actually manufactured in Example 1, which is schematically shown in FIG. 1. The upper photograph of FIG. 3 shows a part of the cross-section of the tablet according to Example 1, and the lower photograph of the same figure is enlargement of a part of the upper photograph. When taking the photograph shown in FIG. 3, the tablet to be photographed was cut in half, and the cut section was smoothed by a file to use as a sample for photograph and then photographed using a digital microscope (KEYENCE CORPORATION, VHX-900F). Black spots visually detected in the upper photograph of FIG. 3 are shavings of the file attached when smoothing the cut section of the tablet by the file and thus should not be included in the tablet of the invention of the present application.

In the manufacture of the tablet shown in FIG. 3, corn starches were used as substitutes for an active ingredient or a nutritionally functional ingredient, and the corn starches were mixed with a binder consisting of a gelatin to constitute a nuclear particle. As shown in FIG. 3, it is revealed that particles of corn starches (equivalent to inclusion particles) are dispersed in the gelatin constituting the first region. Three compositions having close average external diameters on the image were randomly selected from a plurality of the granulated compositions confirmed in the cross-section photograph of the tablet shown in FIG. 3, and the number of corn starch particles (inclusion particles) included in the nuclear particle constituting respective compositions was visually counted on the cross-section photograph. As a result, the number of inclusion particles included in the region of the first nuclear particle was 2230, the number of inclusion particles included in the region of the second nuclear particle was 2512, and the number of inclusion particles included in the region of the third nuclear particle was 2780. Thus, the variation of the number of inclusion particles included in an individual nuclear particle was "75641" when expressed in the dispersion.

When a mixture including the conventional coating granular particles is compressed, a dissolution control layer is deformed or destroyed by a compression force, thereby failing to obtain the dissolution property as initially designed. For preventing it and producing a tablet having sufficient hardness and compactability, the selection of an excipient, a disintegrant, a tablet binder, and a lubricant, and a further strict process management system are required. On the other hand, when the particles of the present application are compressed, the nuclear particle, even when it is deformed, originally has a flexible shape and thus is less likely to be affected by the dissolution effect by deformation, and accordingly the dissolution controlling property is kept. As a result, the flexibility in the selection of an excipient, a disintegrant, a tablet binder, and a lubricant is increased and a strict process management is not required.

Comparative Example 1

Figure 5:
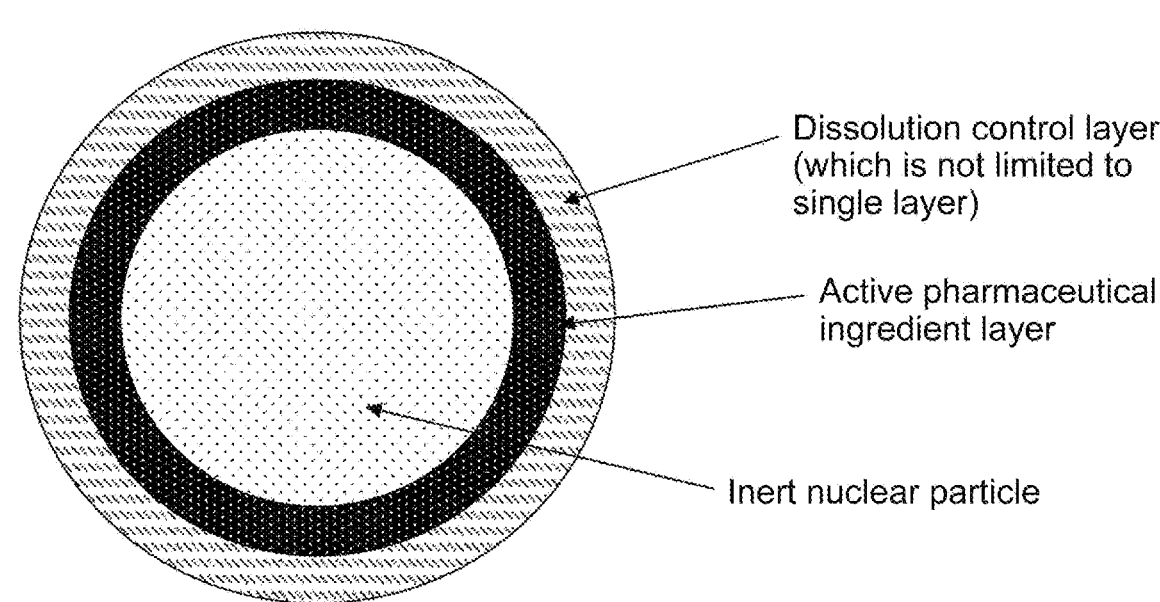
FIG. 5 is a conceptual diagram showing a cross-section structure of a granule of a conventional technique as a granulated composition to be used for tableting, wherein the granule is obtained by coating the outer surface of an inert nuclear particle as an excipient with an active pharmaceutical ingredient and further coating a dissolution control layer thereon (in the case where the nuclear particle surface is ideal spherical).
Figure 6:
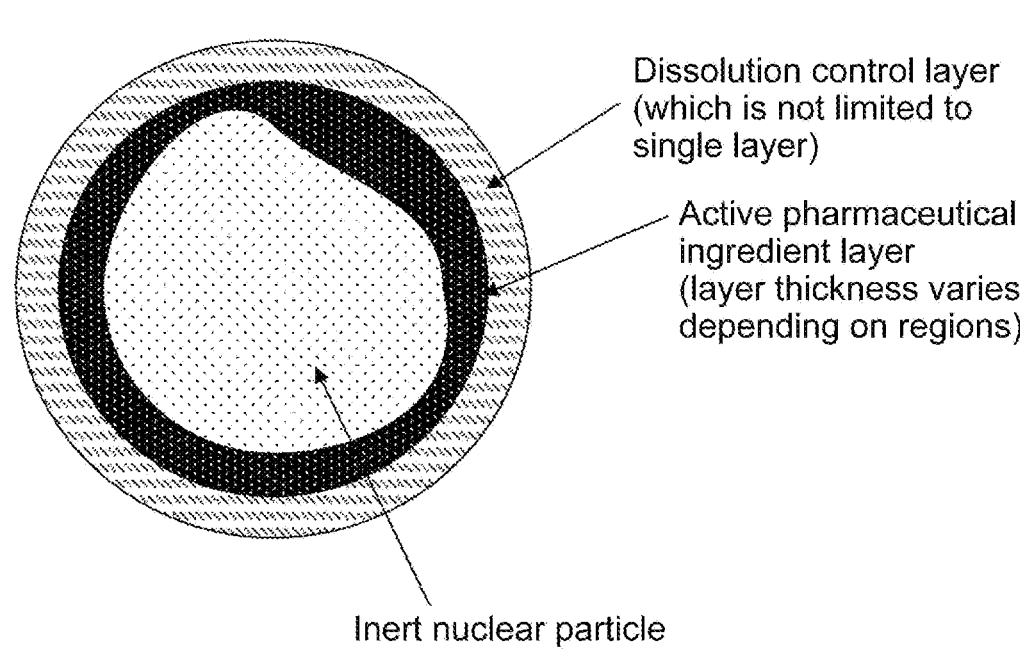
FIG. 6 is a conceptual diagram showing the cross-section structure of a granule of a conventional technique as a granulated composition to be used for tableting, wherein the granule is obtained by coating the outer surface of an inert nuclear particle as an excipient with an active pharmaceutical ingredient and further coating a dissolution control layer thereon (in the case of using a nuclear particle in which the surface shape of the nuclear particle is distorted and lacks the sufficient sphericity). In this case, the amount of an active pharmaceutical ingredient in the active pharmaceutical ingredient layer to be coated fluctuates depending on the surface shape of the nuclear particle, making it difficult to control the amount of an active pharmaceutical ingredient included in an individual granular particle. When an active pharmaceutical ingredient layer or a dissolution control layer is observed as a definite coating layer from a torn surface of the tablet and each nuclear particle has low sphericity, the total amount of the active pharmaceutical ingredient layer to be coated on the outer surface of the nuclear particle varies. In other words, an active pharmaceutical ingredient content in every individual granular particle varies.
Figure 7:
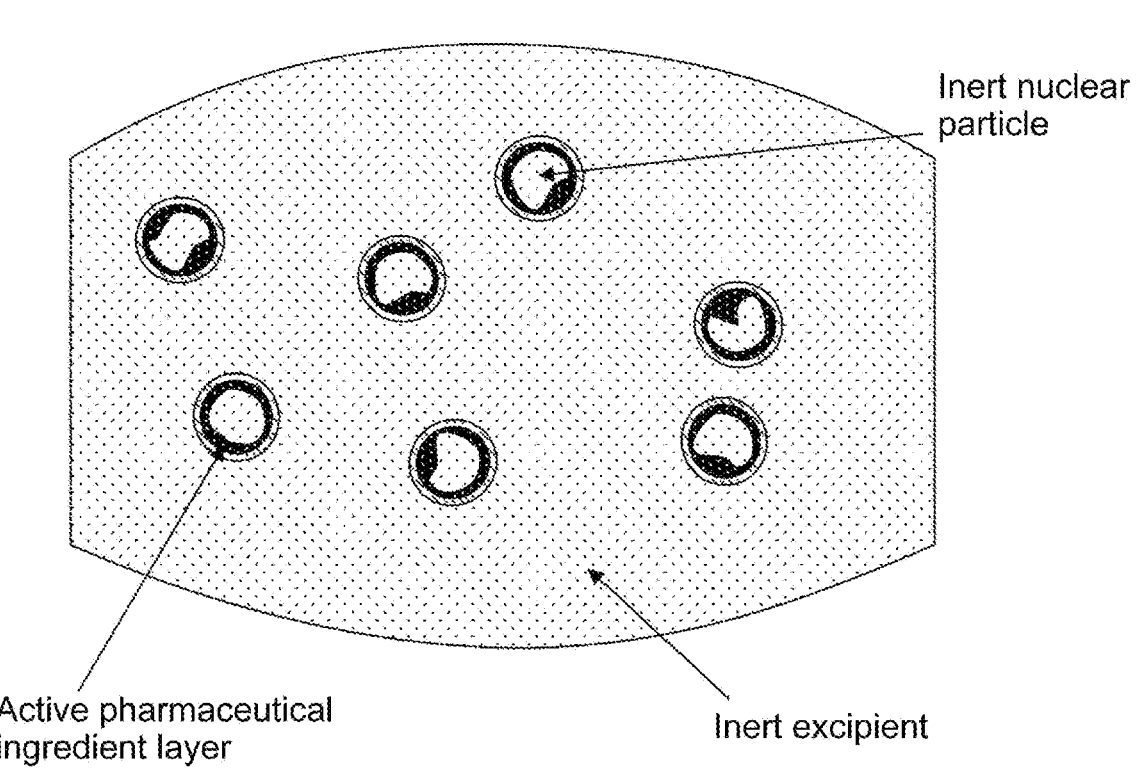
FIG. 7 is a conceptual diagram showing a cross-section structure of a tablet when the tablet is compressed by use of a granulated composition using nuclear particles (coating granular particles) lacking the sufficient sphericity as shown in FIG. 6.

FIG. 5 and FIG. 6 are conceptual diagrams showing the cross-section structures of a conventional granule, as a granulated composition used for compressing, obtained by coating the outer surface of an inert nuclear particle as an excipient with an active pharmaceutical ingredient and further coating a dissolution control layer thereon. FIG. 7 is a conceptual diagram showing the cross-section structure of a tablet when the tablet is compressed by use of a granulated composition using nuclear particles lacking the sufficient sphericity as shown in FIG. 6.

As shown in FIG. 5 to FIG. 7, the region in which active ingredient or biofunctional ingredient is contained forms a layer on the outer surface of the inert nuclear particle and presents as a coating layer to detach the inert nuclear particle as an excipient from the mixture obtained by homogeneously mixing an excipient, a disintegrant, a binder, a lubricant and the like.

Figure 8:
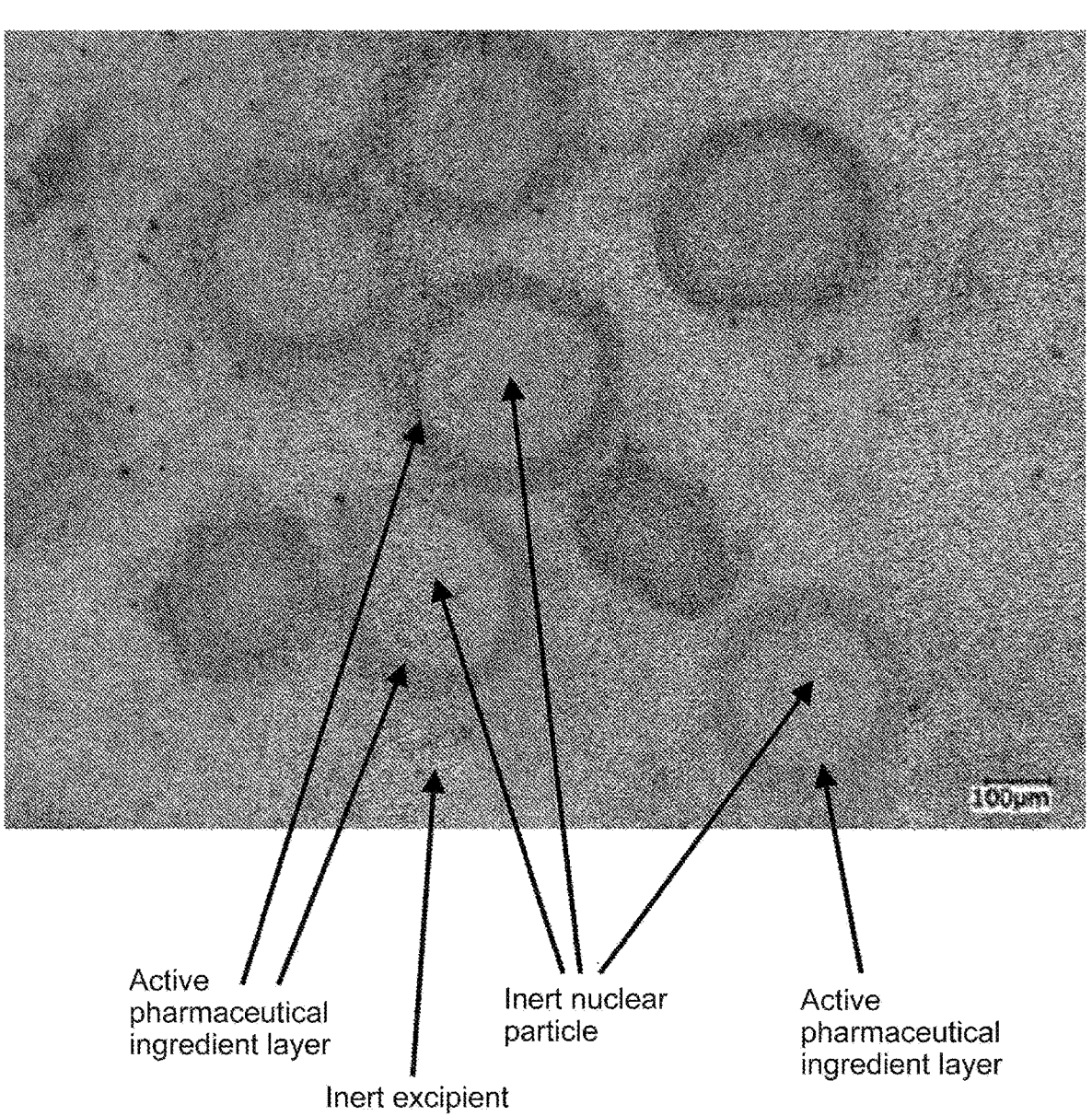
FIG. 8 is a photograph of the cross-section of an actual tablet as of the conventional tablet, which is schematically shown in FIG. 7.

FIG. 8 is a photograph of the cross-section of an actual tablet for the conventional tablet, which is schematically shown in FIG. 7. The photograph was taken by the same method as in Example 2. The upper photograph of FIG. 8 shows a part of the cross-section of the tablet, and the lower photograph of the same figure is enlargement of a part of the upper photograph. When taking the photograph shown in FIG. 8, the tablet to be photographed was cut in half, and the cut section was smoothed by a file to use as a sample for photograph and then photographed using a digital microscope (KEYENCE CORPORATION, VHX-900F). Black spots visually detected in the upper photograph of FIG. 8 are shavings of the file attached when smoothing the cut section of the tablet by the file and thus should not be included in the tablet of Comparative Example 1.

As visually detected in the photograph of FIG. 8, the active pharmaceutical ingredient layer is formed on the outer surface of the inert nuclear particle and presents as a coating layer to detach the inert nuclear particle as an excipient from the mixture obtained by homogeneously mixing an excipient, a disintegrant, a binder, a lubricant and the like. In other words, the conventional tablet shown in FIG. 8 has an unstable total amount of an active pharmaceutical ingredient included therein when the sphericity of granular nuclear particle used for compressing is low.

Three compositions having close average external diameters on the image were randomly selected from a plurality of the granulated compositions confirmed in the cross-section photograph of the tablet shown in FIG. 8, and the number of pixels of the active pharmaceutical ingredient layer surrounding the outer circumference of the nuclear particle constituting respective compositions on the image (in other words, equivalent to an area of the active pharmaceutical ingredient layer on the screen display) was confirmed. Specifically, the active pharmaceutical ingredient layer surrounding the outer circumference of the nuclear particle on the cross-section photograph was extracted by an image processing software, JTrim Version 1.53c (http://www.woodybells.com/jtrim.html), and the number of pixels in the region of the extracted active pharmaceutical ingredient layer was counted by a pixel number calculation software, Pixel Counter version 1.00 (https://www.vector.co.jp/soft/win95/art/se385899.html). As a result, the above confirmation on pixel numbers found that the number of pixels of the active pharmaceutical ingredient layer surrounding the outer circumference of the first nuclear particle was "3132", the number of pixels of the active pharmaceutical ingredient layer surrounding the outer circumference of the second nuclear particle was "2836", and the number of pixels of the active pharmaceutical ingredient layer surrounding the outer circumference of the third nuclear particle was "3425". Thus, the variation of the number of pixels of the active pharmaceutical ingredient layer surrounding the outer circumference of an individual nuclear particle was "86731" when expressed in the dispersion (standard deviation). It is revealed that the obtained dispersion value is a far greater value than the dispersion of the number of inclusion particles (equivalent to an active pharmaceutical ingredient amount) included in each granulated composition constituting the tablet according to Example 1 of the present invention.

In other words, it is revealed that the granulated composition according to the invention of the present application can significantly stabilize the amount of an active pharmaceutical ingredient contained in every granulated composition in comparison with the conventional production method in which the outer circumferential surface of a nuclear particle is coated with an active pharmaceutical ingredient and the like. The amount of the active ingredient or biofunctional ingredient included in the nuclear particle in the granulated composition according to the present invention can be easily adjusted with high accuracy by controlling the volume of a droplet of the nuclear particle solution, manufactured by thoroughly stirring and mixing the binder and the active ingredient or biofunctional ingredient, to be discharged (discharge amount), and this was also confirmed from the actual cut section photograph.

Thus, it is revealed that each granulated composition constituting the tablet according to the present invention can maintain a constant amount of the active ingredient or biofunctional ingredient included in respective nuclear particles without particular efforts and costs of processing for maintaining the sphericity during the production of nuclear particles thereof (in other words, in the case of low sphericity of nuclear particles). On the other hand, in the case of conventional production method in which the outer circumferential surface of the nuclear particle is coated with an active pharmaceutical ingredient layer, it was revealed that, when particular efforts and costs of processing for maintaining the sphericity were not made during the production of nuclear particles thereof and the sphericity thereof was low, the amount of the active ingredient or biofunctional ingredient included in respective nuclear particles was in a significant variation when compared with the granulated composition according to the present invention.

The nuclear particle shown in FIG. 2 has the active ingredient or biofunctional ingredient dispersed in the binder in a particle state, which is however not limited thereto and, for example, the nuclear particle can also be made into a state in which, needless to say, the active ingredient or biofunctional ingredient is dissolved in the binder.

Evaluation on Masking Effect of the Granulated Composition

Example 3, Comparative Examples 2 to 3

First, using the formulation of Table 3 below, granulated compositions in which solifenacin succinate was employed as the bitter taste compound to be masked were prepared. Table 3 below shows the amount of each ingredient when the whole granulated composition manufactured as a result in a dry state is 100%.

TABLE 3

| Solifenacin succinate-containing granulated composition | | | |
|---|---|---|---|
| | Example 3 [wt %] | Comparative Example 2 [wt %] | Comparative Example 3 [wt %] |
| Solifenacin succinate | 20.0 | 10.0 | 20.0 |
| Succinylated monoglycerides | 75.0 | — | — |
| Gelatin | — | 45.0 | — |
| Hardened oil | — | — | 75.0 |
| Corn starch | 5.0 | 45.0 | 5.0 |

Example 3

First, the granulated composition according to Example 3 was manufactured by the applicant of the present application based on the method below. Namely, a sol solution of succinylated monoglyceride (melting point 70° C.) including solifenacin succinate in a state of amorphous was prepared under a condition of about 80° C. so that the granulated composition to be manufactured as a result could have, after dried, the composition shown in Example 3 of Table 3 (provided that corn starch was excluded), and discharged as droplets having a size of a diameter of about 0.3 mm to a rolling cooling medium (Japanese Pharmacopoeia corn starch) at room temperature (example: 23° C.). These droplets, after cooled and solidified, were classified using a 140-mesh sieve.

Comparative Example 2

The granulated composition according to Comparative Example 2 was manufactured by the applicant of the present application based on the method below. Namely, a sol solution of gelatin was prepared under a condition of about 65° C. so that the granulated composition to be manufactured as a result could have, after dried, the composition shown in Comparative Example 2 of Table 3 (provided that corn starch was excluded), and discharged as droplets having a size of a diameter of about 0.3 mm to a rolling cooling medium (Japanese Pharmacopoeia corn starch) at room temperature (example: 23° C.). These droplets, after cooled and solidified, were classified using a 140-mesh sieve.

Comparative Example 3

The granulated composition according to Comparative Example 3 was manufactured by the applicant of the present application based on the method below. Namely, a sol solution of a hardened oil was prepared under a condition of about 80° C. so that the granulated composition to be manufactured as a result could have, after dried, the composition shown in Comparative Example 3 of Table 3 (provided that corn starch was excluded), and discharged as droplets having a size of a diameter of about 0.3 mm to a rolling cooling medium (Japanese Pharmacopoeia corn starch) at room temperature (example: 23° C.). These droplets, after cooled and solidified, were classified using a 140-mesh sieve.

Examples 4 to 7, Comparative Examples 4 to 5

Subsequently, using Table 4 below, the formulation of granulated compositions in which quinine hydrochloride was employed as a bitter taste compound is described. Table 4 below shows the amount of each ingredient when the whole granulated composition manufactured as a result in a dry state is 100%.

TABLE 4

| Quinine hydrochloride-containing granulated composition | | | | | | |
|---|---|---|---|---|---|---|
| | Example 4 [wt %] | Example 5 [wt %] | Example 6 [wt %] | Example 7 [wt %] | Comparative Example 4 [wt %] | Comparative Example 5 [wt %] |
| Quinine hydrochloride | 5.0 | 20.0 | 30.0 | 40.0 | 30.0 | 20.0 |
| Succinylated monoglycerides | 90.0 | 75.0 | 65.0 | 55.0 | — | — |
| Tartaric acid esters of monoglycerides | — | — | — | — | 65.0 | — |
| Hardened oil | — | — | — | — | — | 75.0 |
| Corn starch | 5.0 | 5.0 | 5.0 | 5.0 | 5.0 | 5.0 |

Examples 4 to 7

The granulated compositions according to Examples 4 to 7 were manufactured by the applicant of the present application based on the method below. Namely, sol solutions of succinylated monoglyceride including quinine hydrochloride in a state of amorphous were prepared under a condition of about 80° C. so that the granulated compositions to be manufactured as a result could have, after dried, the compositions shown in Examples 4 to 7 of Table 4 (provided that corn starch was excluded), and discharged as droplets having a size of a diameter of about 0.3 mm to a rolling cooling medium (Japanese Pharmacopoeia corn starch) at room temperature (example: 23° C.). These droplets, after cooled and solidified, were classified using a 140-mesh sieve.

Comparative Example 4

The granulated composition according to Comparative Example 4 was manufactured by the applicant of the present application based on the method below. Namely, a sol solution of tartaric acid esters of monoglyceride including quinine hydrochloride in a state of amorphous was prepared under a condition of about 80° C. so that the granulated composition to be manufactured as a result could have, after dried, the composition shown in Comparative Example 4 of Table 4 (provided that corn starch was excluded), and discharged as droplets having a size of a diameter of about 0.3 mm to a rolling cooling medium (Japanese Pharmacopoeia corn starch) at room temperature (example: 23° C.). These droplets, after cooled and solidified, were classified using a 140-mesh sieve.

Comparative Example 5

The granulated composition according to Comparative Example 5 was manufactured by the applicant of the present application based on the method below. Namely, a sol solution of a hardened oil including quinine hydrochloride in a state of amorphous was prepared under a condition of about 80° C. so that the granulated composition to be manufactured as a result could have, after dried, the composition shown in Comparative Example 5 of Table 4 (provided that corn starch was excluded), and discharged as droplets having a size of a diameter of about 0.3 mm to a rolling cooling medium (Japanese Pharmacopoeia corn starch) at room temperature (example: 23° C.). These droplets, after cooled and solidified, were classified using a 140-mesh sieve.

Although examples using a powder bed as the cooling medium are shown in the methods for producing the granulated composition as described above, the cooling medium is not limited thereto as long as medium has no compatibility with the nuclear particle solution and, for example, fats and oils and air, needless to say, can be employed as the cooling medium.

Thus, the granulated compositions of the invention of the present application contained particulate nuclear particles consisting of glycerin fatty acid ester (the masking agent having a masking function of the predetermined compounds) and solifenacin succinate and/or quinine hydrochloride (the predetermined compound), which is masked by the glycerin fatty acid ester and at least a part of which is included in the masking agent in a state of amorphous.

Examples of the method for identifying the crystal structure of solifenacin succinate or a salt thereof include, but are not particularly limited to, polarization microscope observation method, X-ray diffraction analysis, DSC measurement method, and near infrared spectroscopy. For example, in the case of evaluating using the XRD method, it is determined that solifenacin succinate or a salt thereof is complete amorphous when no specific peak derived from the crystalline solifenacin found at near $2\theta=10°$ C. is detected, however the result changes to a certain extent depending on measurement conditions and hence should not be interpreted too strictly.

In Examples 3, 8, 9, 10, and 11, a polarizing filter was installed in a phase-contrast microscope MT5210L manufactured by Meiji Techno Co., Ltd. to compare the degrees of crystalline birefringence by the polarization microscope observation method. The degree of birefringence of granulated composition described above was smaller than the degree of birefringence observed when the predetermined compound in the same amount was examined using the microscope, thereby it was determined that at least a part thereof was amorphous.

Moreover, in the invention of the present application, solifenacin succinate or quinine hydrochloride as the bitter taste compound is melted in the glycerin fatty acid ester as a bitter taste inhibitor in the amount which is equal to or less than the solubility of solifenacin succinate or quinine hydrochloride in the glycerin fatty acid ester included in the nuclear particle.

Japanese Pharmacopoeia corn starch (coating particles having a smaller particle diameter than that of the nuclear particles) is attached as a coating material (powder coat) around the nuclear particle consisting of the predetermined compound and the glycerin fatty acid ester. Here, the "coating" is not limited to the case of coating throughout the entire outer surface of the nuclear particle but includes the case where a part of the outer surface of the nuclear particle is exposed in gaps between the coating particles.

(Evaluation of the Bitter Taste Masking Effect)

The degrees of masking effect of the granulated composition in each Example and Comparative Example in the above Tables were as follows (bitter taste evaluation). Here, the bitter taste evaluation is made by a so-called sensory evaluation. Specifically, the evaluation was carried out by scoring the degree of bitter taste. Evaluators hold the manufactured granulated composition in the mouth and keep it on the tongue for 60 seconds to subjectively score the degree of bitter taste sensed. Specifically, the degrees of the bitter taste were classified as a 4-point scale of 1 to 4, in which five panelists were asked to select any of "4: It is so numbing bitter that immediate spitting out was urged", "3. Intense bitterness was sensed but not as much as spitting out", "2. Sensed bitterness but can be toned down with sweetness", and "1. Substantially no bitterness was sensed", and a score average value was calculated.

As the results of the bitter taste evaluations by the 5 evaluation panelists regarding Example 3, Comparative Example 2, and Comparative Example 3 (Table 3) in which solifenacin succinate was used as the bitter taste compound, Example 3 had a score average value by 5 panelists of 1.5, which shows that the bitter taste of solifenacin succinate was masked. On the other hand, Comparative Examples 2 and 3 had a score average value by 5 panelists of 3.3, which shows that the bitter taste of solifenacin succinate could not be masked.

Moreover, regarding Examples 4 to 7 and Comparative Examples 4 and 5 (Table 4) in which quinine hydrochloride was used as the bitter taste compound, Examples 4 to 6 had a score average value by 5 panelists of 1.0, which shows that the bitter taste of quinine hydrochloride was masked. Example 7 had a score average value by 5 panelists of 2.2, which shows that the masking ability was slightly lower than that of Examples 4 to 6. On the other hand, Comparative Examples 4 and 5 had a score average value by 5 panelists of 2.8, which shows that the bitter taste of quinine hydrochloride could not be masked.

(Results of Verification)

As described above, as a result of intensive research by the inventors of the invention of the present application, according to the present invention, it was confirmed that the bitter taste could be masked even when solifenacin succinate as the bitter taste compound was included up to 20% to the whole granulated composition. Moreover, according to the present invention, it was confirmed that the bitter taste could be masked even when quinine hydrochloride as the bitter taste compound was included up to 30% to the whole granulated composition.

The coating material coating the above nuclear particle can also be used as a coating agent which coats the outer surface of the nuclear particle.

Moreover, the bitter taste compound which may be used in the present Examples is not limited to quinine hydrochloride and solifenacin succinate described as examples and, for example, eszopiclone (for example, the content of which is 5% or less of the whole granulated composition) can also be employed. It is obviously not limited to the case where the above quinine hydrochloride, solifenacin succinate, eszopiclone, and the like are contained singly, and the bitter taste compounds can also be composed of any two of these or the combination of all.

Further, although the present Examples show the case where the compound to be masked is bitter taste compounds (in other words, the predetermined characteristic to be masked is "bitter taste"), the compounds to be masked are not limited thereto. The masking technique according to the present invention is, needless to say, applicable to any compound having characteristics to be masked.

Dissolution Test

Examples 3, 8 to 11, Comparative Example 6

Following the formulations shown in Table 5 below, granulated compositions in which solifenacin succinate was employed as the bitter taste compound to be masked were prepared. Table 5 below shows the amount of each ingredient when the whole granulated composition manufactured as a result in a dry state is 100%.

dried, the composition shown in Example 8 of Table 5 (provided that corn starch was excluded), and discharged as droplets having a size of a diameter of about 0.3 mm to a rolling cooling medium (Japanese Pharmacopoeia corn starch) at room temperature (example: 23° C.). These droplets, after cooled and solidified, were classified using a 140-mesh sieve.

Example 9

The granulated composition according to Example 9 was manufactured by the applicant of the present application based on the method below. Namely, a sol solution of decaglycerin behenic acid ester in which a part of solifenacin succinate was included in a state of amorphous was prepared under a condition of about 80° C. so that the granulated composition to be manufactured as a result could have, after dried, the composition shown in Example 9 of Table 5 (provided that corn starch was excluded), and discharged as droplets having a size of a diameter of about 0.3 mm to a rolling cooling medium (Japanese Pharmacopoeia corn starch) at room temperature (example: 23° C.). These droplets, after cooled and solidified, were classified using a 140-mesh sieve.

Example 10

The granulated composition according to Example 10 was manufactured by the applicant of the present application based on the method below. Namely, a sol solution of sorbitan monostearate in which a part of solifenacin succinate was included in a state of amorphous was prepared

TABLE 5

| | Example 3 | Example 8 [wt %] | Example 9 [wt %] | Example 10 [wt %] | Example 11 [wt %] | Comparative Example 6 [wt %] |
|---|---|---|---|---|---|---|
| Solifenacin succinate | 20 | 20 | 20 | 20 | 20 | 20 |
| Citric acid esters of Monoglycerides (Melting point 59° C.) | 75 | — | — | — | — | — |
| Polyglycerin fatty acid ester 1 (Melting point 65° C.) | | 75 | — | — | — | — |
| Polyglycerin fatty acid ester 2 (Melting point 77° C.) | | — | 75 | — | — | — |
| Sorbitan monostearate (Melting point 60° C.) | | — | — | 75 | — | — |
| Polyethylene glycol 4000 (Melting point 55° C.) | | — | — | — | 75 | — |
| Glycerin fatty acid ester (Melting point 82° C.) | | — | — | — | — | 75 |
| Corn starch | 5 | 5 | 5 | 5 | 5 | 5 |

Solifenacin succinate-containing granulated composition

Example 8

The granulated composition according to Example 8 was manufactured by the applicant of the present application based on the method below. Namely, a sol solution of decaglycerin stearic acid ester in which a part of solifenacin succinate was included in a state of amorphous was prepared under a condition of about 80° C. so that the granulated composition to be manufactured as a result could have, after under a condition of about 80° C. so that the granulated composition to be manufactured as a result could have, after dried, the composition shown in Example 10 of Table 5 (provided that corn starch was excluded), and discharged as droplets having a size of a diameter of about 0.3 mm to a rolling cooling medium (Japanese Pharmacopoeia corn starch) at room temperature (example: 23° C.). These droplets, after cooled and solidified, were classified using a 140-mesh sieve.

Example 11

The granulated composition according to Example 11 was manufactured by the applicant of the present application based on the method below. Namely, a sol solution of polyethylene glycol 4000 in which a part of solifenacin succinate was included in a state of amorphous was prepared under a condition of about 80° C. so that the granulated composition to be manufactured as a result could have, after dried, the composition shown in Example 11 of Table 5 (provided that corn starch was excluded), and discharged as droplets having a size of a diameter of about 0.3 mm to a rolling cooling medium (Japanese Pharmacopoeia corn starch) at room temperature (example: 23° C.). These droplets, after cooled and solidified, were classified using a 140-mesh sieve.

Comparative Example 6

The granulated composition according to Comparative Example 6 was manufactured by the applicant of the present application based on the method below. Namely, a sol solution of glycerin monobehenate in which a part of solifenacin succinate was included in a state of amorphous was prepared under a condition of about 80° C. so that the granulated composition to be manufactured as a result could have, after dried, the composition shown in Comparative Example 6 of Table 5 (provided that corn starch was excluded), and discharged as droplets having a size of a diameter of about 0.3 mm to a rolling cooling medium (Japanese Pharmacopoeia corn starch) at room temperature (example: 23° C.). These droplets, after cooled and solidified, were classified using a 140-mesh sieve.

(Evaluation of Dissolution Property)

A dissolution test on the granulated composition of Example 3 was carried out to evaluate masking conditions of the bitter taste compound.

The dissolution test was carried out by the conditions below.

Dissolution tester: Toyama Dissolution Tester NTR-6400A

Dissolution test conditions: 5 mg of bitter taste compound/900 mL of dissolution solution, 50 rpm 37° C., paddle method For the dissolution solution, purified water was used.

A concentration of bitter taste compound in the dissolution solution was quantitatively determined by HPLC and dissolution rates were compared.

HPLC: pump LC-20AD, autosampler SIL-20A, controller CBM-20A

UV Detector SPD-20A, column oven CTO-20A (Shimadzu Corporation)

The evaluation of dissolution property of the granulated composition was carried out by comparing the granulated composition including the bitter taste composition used in Example 3 with 5 mg of Vesicare (registered trademark) OD tablet (Astellas Pharma Inc.). The active ingredient-containing granule in 5 mg of Vesicare OD tablet had the structure as shown in FIG. 5, and the active ingredient layer was found on the cross-section thereof.

Figure 4:
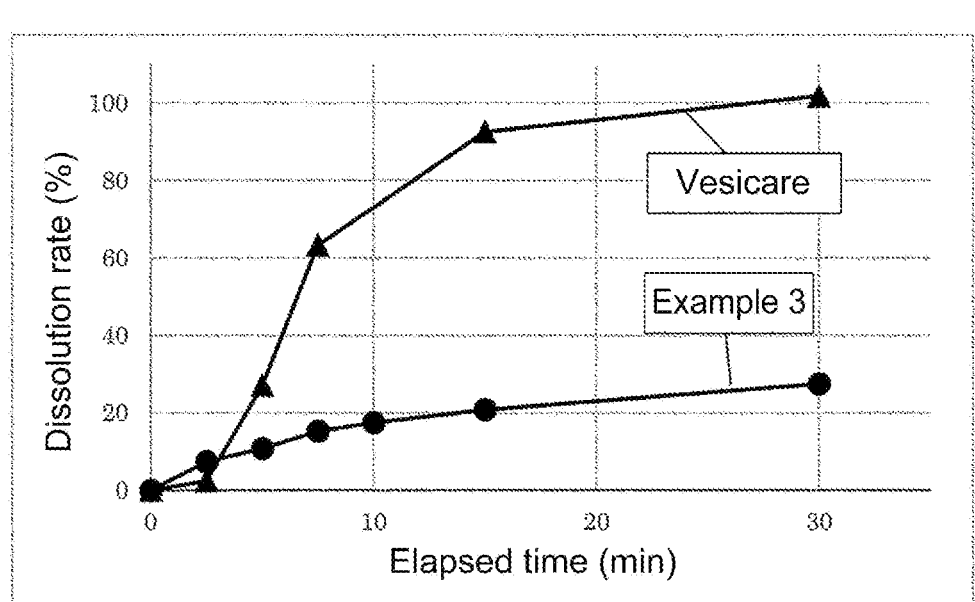
FIG. 4 is a figure comparing the dissolution rate of the granulated composition of the present application with the dissolution rate of Vesicare.

FIG. 4 is a graph showing the relation between the elapsed time (min) from the start of test and the dissolution rate (%). According to the graph shown in FIG. 4, the substantially full amount of the bitter taste composition in 5 mg of Vesicare OD tablet was dissolved out when 30 minutes had passed, whereas only less than 30% of the bitter taste composition in Example 3 was dissolved. This shows that the granulated composition of Example 3 inhibits the dissolution of the bitter taste composition more than the prior art and has a higher bitter taste masking effect.

(Sensory Test of Masking Effect)

A sensory test on the granulated composition of Example 3 was carried out to evaluate masking conditions of the bitter taste compound.

The sensory test was carried out by the method below.

The granulated composition of Example 3 containing 5 mg of the bitter taste compound and one Vesicare 5 mg tablet were given to 5 test subjects. An interview was conducted regarding the bitter taste sensed when the test sample (the above granulated composition of Example 3 or Vesicare tablet) was kept in the mouth for 30 seconds.

The results of the sensory test are shown in Table 6. The meanings of the symbols in Table are as follows.

○: Sensed that the granulated composition according to Example 3 had less bitterness compared with the Vesicare tablet.

Δ: Sensed no difference between the granulated composition according to Example 3 and the 5 mg Vesicare tablet.

x: Sensed that the Vesicare 5 mg tablet had less bitterness compared with the granulated composition according to Example 3.

Table 6 below shows that the composition of Example 3 has a higher masking effect than the 5-mg Vesicare OD tablet.

TABLE 6

| Results of sensory test | |
| --- | --- |
| Test subject 1 | Δ |
| Test subject 2 | ○ |
| Test subject 3 | ○ |
| Test subject 4 | Δ |
| Test subject 5 | ○ |

Subsequently, an oral disintegrating tablet having the composition of Table 7 below was manufactured for evaluating the oral disintegrating tablet manufactured using the granulated composition according to Example 3.

(Manufacture of an Oral Disintegrating Tablet)

Each ingredient shown in Table 7 below was weighed, put and sealed in a 40 cm×70 cm clear polyethylene bag, mixed by inverting by hand for 10 minutes to prepare a mixed powder for compressing, and a round flat oral disintegrating tablet (diameter 7 mm, weight per tablet 120 mg) was produced using a rotary tablet press machine (PICCOLA D8).

(Evaluation of Feeling on the Tongue of a Manufactured Oral Disintegrating Tablet)

Using the granulated composition (granules) obtained in the above Example 3, an oral disintegrating tablet having the composition shown in Table 7 was produced by the method below. The feeling on the tongue of the obtained oral disintegrating tablet was evaluated by five panelists. In the evaluation, five panelists determined whether the granulated composition of the present invention caused an unpleasant rough feel when the oral disintegrating tablet disintegrated in the oral cavity without taking water. In all the panelists, this oral disintegrating tablet disintegrated in the oral cavity in about 50 to 65 seconds, and neither hard grain feel nor an unpleasant rough feel was sensed in the oral cavity during and after disintegration.

TABLE 7

| Composition of oral disintegrating tablet | | | |
|---|---|---|---|
| | Per tablet (mg) | Feed weight (g) | Percentage (%) |
| Granulated composition of Example 3 | 12 | 6 | 10.00% |
| Pregelatinized starch ("Swel Star PD1" manufactured by Asahi Kasei Chemicals Corporation) | 4 | 2 | 3.33% |
| D-Mannitol ("Granutol R" manufactured by Freund Corporation) | 75 | 37.5 | 62.50% |
| Crystalline cellulose ("CEOLUS ST100" manufactured by Asahi Kasei Corporation) | 20.6 | 10.3 | 17.17% |
| Light anhydrous silicic acid ("Adsolider 101" manufactured by Freud Corporation) | 1.8 | 0.9 | 1.50% |
| Crospovidone ("Kollidon CL-F" manufactured by BASF) | 3.6 | 1.8 | 3.00% |
| Hydroxypropyl cellulose ("HPC-SSL-SFP" manufactured by NIPPON SODA CO., LTD.) | 1.2 | 0.6 | 1.00% |
| Aspartame ("PAL SWEET" manufactured by Ajinomoto Co., Inc.) | 0.6 | 0.3 | 0.50% |
| Magnesium stearate (manufactured by TAIHEI CHEMICAL INDUSTRIAL CO., LTD.) | 1.2 | 0.6 | 1.00% |
| Total | 120 | 60 | 100.00% |

<Evaluation of Friability>

The tablet compressed using the granulated composition according to Example 3 manufactured as described above was evaluated for the friability based on Japanese Pharmacopoeia (http://jpdb.nihs.go.jp/jp14/pdf/1237-1.pdf) using an Electrolab friability tester, EF-2. Fifty-five tablets (about 6.6 g) were put in a clear plastic drum having an inner diameter of 287 mm and a depth of about 38 mm and rotated 100 times at a rate of 25 rpm. After the rotation, the tablets were taken out and observed. As a result, no tablet cracking or chipping was detected, and the friability determined from the changes of tablet weight before and after the test was 0.1%.

The present invention includes the tablets and the methods as described in (1) to (33) below.

(1) A tablet obtained by compressing a mixture including at least a granulated composition including an active ingredient or a biofunctional ingredient, wherein the tablet comprises a first region consisting of a binder including an active ingredient or a biofunctional ingredient, and a second region adjacent to the first region and consisting of the binder including the active ingredient or a biofunctional ingredient, wherein the active ingredient or biofunctional ingredient included in the first region and the second region is dispersed without forming a layer in the region in which each of the active ingredient or biofunctional ingredient is included.

(2) The tablet according to (1), wherein the binder consists of an inert substance.

(3) The tablet according to (1) or (2), wherein the inert substance is at least any of gelatin, carrageenan, agar, polyethylene glycol, methyl cellulose, hydroxypropyl methylcellulose, hydroxypropyl cellulose, a methacrylate copolymer, an aminoalkyl methacrylate copolymer, an ammonio alkyl methacrylate copolymer, an ethyl acrylate-methyl methacrylate copolymer, hypromellose phthalate, hypromellose acetate succinate, cellulose acetate phthalate and polyvinyl acetate phthalate, and a hardened oil or a surfactant having a melting point of 80° C. or less.

(4) The tablet according to any of (1) to (3) further comprising a coating layer which coats an outer surface of each of the first region and the second region and is composed of a substance insoluble in the binder.

(5) The tablet according to (4), wherein the coating layer is composed of coating particles having an aspect ratio of 10 or less.

(6) A tablet obtained by compressing a mixture including at least a granulated composition including an active ingredient or a biofunctional ingredient, wherein the tablet comprises a first region consisting of a binder including an active ingredient or a biofunctional ingredient, and a second region adjacent to the first region and consisting of the binder including the active ingredient or a biofunctional ingredient, wherein the active ingredient or biofunctional ingredient included in the first region and the second region is dissolved without forming a layer in the region in which each of the active ingredient or biofunctional ingredient is included.

(7) The tablet according to (6), wherein the binder consists of an inert substance.

(8) The tablet according to (6) or (7), wherein the inert substance is at least any of gelatin, carrageenan, agar, polyethylene glycol, methyl cellulose, hydroxypropyl methylcellulose, hydroxypropyl cellulose, a methacrylate copolymer, an aminoalkyl methacrylate copolymer, an ammonio alkyl methacrylate copolymer, an ethyl acrylate-methyl methacrylate copolymer, hypromellose phthalate, hypromellose acetate succinate, cellulose acetate phthalate and polyvinyl acetate phthalate, and a hardened oil or a surfactant having a melting point of 80° C. or less.

(9) The tablet according to any of (6) to (8) further comprising a coating layer which coats an outer surface of each of the first region and the second region and is composed of a substance insoluble in the binder.

(10) The tablet according to (9), wherein the coating layer is composed of coating particles having an aspect ratio of 10 or less.

(11) A tablet obtained by compressing a mixture including at least a granulated composition containing an active ingredient or biofunctional ingredient, wherein the granulated composition has inclusion particles, coating particles, and a binder retaining a granular figure by binding the inclusion particles with each other and the inclusion particles with the coating particles, the coating particles are attached around the nuclear particle consisting of the inclusion particles and the binder in which the coating particles are insoluble in the binder, the active ingredient or biofunctional ingredient is contained in the inclusion particles and/or the binder, and a developed interfacial area ratio Sdr is 100 to 700.

(12) The tablet according to (11), wherein the coating particles have an aspect ratio of 10 or less.

(13) A method for producing a tablet comprising mixing a granulated composition including an active ingredient or biofunctional ingredient with other substances to be mixed, and compressing the mixture obtained by the mixing, wherein the granulated composition has inclusion particles, coating particles, and a binder retaining a granular figure by binding the inclusion particles with each other and the inclusion particles with the coating particles, the coating particles are attached around the nuclear particle consisting of the inclusion particles and the binder in which the coating particles are insoluble in the binder, the active ingredient or biofunctional ingredient is contained in the inclusion particles and/or the binder, and a developed interfacial area ratio Sdr is 100 to 700.

(14) The method for producing a tablet according to (13), wherein the coating particles have an aspect ratio of 10 or less.

(15) A granulated composition comprising a particulate nuclear particle consisting of a masking agent having a masking function on a predetermined compound and the predetermined compound to be masked by the masking agent, wherein at least a part of the predetermined compound is included in a state of amorphous in the masking agent.

(16) The granulated composition according to (15), wherein the predetermined compound is melted in the masking agent in an amount which is equal to or less than a solubility of the predetermined compound in the masking agent constituting the nuclear particle.

(17) The granulated composition according to (15) or (16), further comprising a coating material coating around the nuclear particle.

(18) The granulated composition according to (17), wherein the coating material is coating particles having a smaller particle diameter than the nuclear particle.

(19) The granulated composition according to (17), wherein the coating material is a coating agent which coats an outer surface of the nuclear particle.

(20) The granulated composition according to any of (15) to (19), wherein the predetermined compound is a bitter taste compound, and
the masking agent is a bitter taste inhibitor for inhibiting bitterness of the bitter taste compound.

(21) The granulated composition according to (20), wherein the bitter taste inhibitor is a glycerin fatty acid ester.

(22) The granulated composition according to (21), wherein the glycerin fatty acid ester is an organic acid ester.

(23) The granulated composition according to (22), wherein the organic acid ester is organic acid monoglyceride.

(24) The granulated composition according to (23), wherein the organic acid monoglyceride is one or two or more selected from succinylated monoglycerides, citric acid esters of monoglycerides, tartaric acid esters of monoglycerides, and acetic acid esters of monoglycerides.

(25) The granulated composition according to any one of (20) to (24), wherein the bitter taste compound is pharmacologically acceptable citric acid salts or succinic acid salts of an active ingredient or biofunctional ingredient.

(26) The granulated composition according to any one of (20) to (24), wherein the bitter taste compound is at least any of solifenacin succinate and quinine hydrochloride.

(27) The granulated composition according to any one of (20) to (24), wherein the nuclear particle includes 20% or less of solifenacin succinate as the bitter taste compound.

(28) The granulated composition according to any one of (20) to (24), wherein the nuclear particle includes 30% or less of quinine hydrochloride as the bitter taste compound.

(29) The granulated composition according to (28), wherein the coating particle is Japanese Pharmacopoeia corn starch.

(30) A method for producing a granulated composition, wherein
a bitter taste compound is mixed while being melted in a bitter taste inhibitor for inhibiting the bitter taste of the bitter taste compound to produce a nuclear particle solution, and
the nuclear particle solution is ejected as droplets toward a predetermined cooling medium having no compatibility with the nuclear particle solution.

(31) The method according to (30), wherein the cooling medium is a powder bed consisting of a powder.

(32) The method according to (30), wherein the cooling medium is an oil and a fat.

(33) The method according to (30), wherein the cooling medium is air.

The embodiments have been described in the above, which are however presented as examples and do not intend to limit the scope of the present invention. These novel embodiments can be carried out in other various forms, and various omissions, replacements, and alterations can be made without departing from the subject matter of the invention. This embodiment and variations thereof are included in the scope and the subject matter of the invention and also included in the inventions described in the scope of the claims and in the range of equivalency thereof.

The invention claimed is:

1. A tablet obtained by compressing a mixture comprising at least one granulated composition comprising a plurality of granules having a developed interfacial area ratio (Sdr) of 100 to 700 and comprising an active ingredient or biofunctional ingredient, wherein each granule comprises:
a nuclear particle comprising a binder and the active ingredient or biofunctional ingredient; and
a coating layer, which coats the nuclear particle, consisting of coating particles insoluble in the binder and having an aspect ratio of 11 or less,
wherein the active ingredient or biofunctional ingredient is dispersed or dissolved without forming a layer in the binder.

2. The tablet according to claim 1, wherein the binder consists of an inert substance.

3. The tablet according to claim 2, wherein the inert substance is selected from the group consisting of glycerin fatty acid ester, gelatin, carrageenan, agar, polyethylene glycol, methyl cellulose, hydroxypropyl methylcellulose, hydroxypropyl cellulose, methacrylate copolymer, aminoalkyl methacrylate copolymer, ammonio alkyl methacrylate copolymer, ethyl acrylate-methyl methacrylate copolymer, hypromellose phthalate, hypromellose acetate succinate, cellulose acetate phthalate, polyvinyl acetate phthalate, a hardened oil having a melting point of 80° C. or less, and a surfactant having a melting point of 80° C. or less.

4. The tablet according to claim 1, wherein at least a part of the active ingredient or biofunctional ingredient is in an amorphous state and is present in the binder.

5. The tablet according to claim 4, wherein the active ingredient or biofunctional ingredient is dispersed in the binder in an amount which is equal to or less than the solubility of the active ingredient or biofunctional ingredient in the binder.

6. The tablet according to claim 4, wherein the active ingredient or biofunctional ingredient is a bitter taste compound, and the binder is a bitter taste inhibitor for inhibiting the bitter taste of the bitter taste compound.

7. The tablet according to claim 6, wherein the bitter taste inhibitor is a glycerin fatty acid ester.

8. The tablet according to claim 7, wherein the glycerin fatty acid ester is an organic acid ester.

9. The tablet according to claim 8, wherein the organic acid ester is an organic acid monoglyceride.

10. The tablet according to claim 9, wherein the organic acid monoglyceride is selected from the group consisting of at least one of a succinylated monoglyceride, a citric acid ester of a monoglyceride, a tartaric acid ester of a monoglyceride, an acetic acid ester of a monoglyceride, and mixtures thereof.

11. The tablet according to claim 6, wherein the bitter taste compound is a pharmaceutically acceptable citric acid salt or a succinic acid salt of the active ingredient or biofunctional ingredient.

12. The tablet according to claim 1, wherein the coating particle is corn starch.

13. A method for producing the tablet of claim 1, the method comprising:

mixing the mixture comprising at least one granulated composition; and compressing the mixture.

14. The method according to claim 13, wherein the binder consists of an inert substance.

15. The method according to claim 14, wherein the inert substance is selected from the group consisting of glycerin fatty acid ester, gelatin, carrageenan, agar, polyethylene glycol, methyl cellulose, hydroxypropyl methylcellulose, hydroxypropyl cellulose, methacrylate copolymer, aminoalkyl methacrylate copolymer, ammonio alkyl methacrylate copolymer, ethyl acrylate-methyl methacrylate copolymer, hypromellose phthalate, hypromellose acetate succinate, cellulose acetate phthalate, polyvinyl acetate phthalate, a hardened oil having a melting point of 80° C. or less, and a surfactant having a melting point of 80° C. or less.

16. The method according to claim 13, wherein at least a part of the active ingredient or biofunctional ingredient is in an amorphous state and is present in the binder.

* * * * *